United States Patent
Taylor et al.

(10) Patent No.: US 8,216,784 B2
(45) Date of Patent: Jul. 10, 2012

(54) CANCER-DERIVED MICROVESICLE-ASSOCIATED MICRORNA AS A DIAGNOSTIC MARKER

(75) Inventors: Douglas D. Taylor, Louisville, KY (US); Cicek Gercel-Taylor, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 12/524,462

(22) PCT Filed: Jul. 25, 2008

(86) PCT No.: PCT/US2008/071235
§ 371 (c)(1),
(2), (4) Date: Jul. 24, 2009

(87) PCT Pub. No.: WO2009/015357
PCT Pub. Date: Jan. 29, 2009

(65) Prior Publication Data
US 2010/0298151 A1    Nov. 25, 2010

Related U.S. Application Data

(60) Provisional application No. 60/951,812, filed on Jul. 25, 2007, provisional application No. 61/050,438, filed on May 5, 2008.

(51) Int. Cl.
*C12Q 1/68* (2006.01)
(52) U.S. Cl. ...................................................... 435/6.1
(58) Field of Classification Search .................. 435/6.1
See application file for complete search history.

(56) References Cited

U.S. PATENT DOCUMENTS

| | | | |
|---|---|---|---|
| 5,089,181 A | 2/1992 | Hauser | |
| 6,812,023 B1 | 11/2004 | Lamparski et al. | |
| 7,897,356 B2 | 3/2011 | Klass et al. | |
| 8,021,847 B2 | 9/2011 | Pietrzkowski | |
| 2003/0036077 A1 | 2/2003 | Chenchik et al. | |
| 2003/0068642 A1 | 4/2003 | Urnovitz | |
| 2005/0158708 A1 | 7/2005 | Alroy et al. | |
| 2007/0059765 A1 | 3/2007 | Wang et al. | |
| 2008/0268429 A1 | 10/2008 | Pietrzkowski | |
| 2009/0011428 A1 | 1/2009 | Nam et al. | |
| 2009/0226887 A1 | 9/2009 | Brisson | |

FOREIGN PATENT DOCUMENTS

| | | |
|---|---|---|
| WO | 2005121369 | 12/2005 |
| WO | 2005121369 A2 | 12/2005 |
| WO | 2009036236 | 3/2009 |

OTHER PUBLICATIONS

Geuze et al., J. Cell Biol, 1988, 107(6): 2491-501.*
Tockman et al., Cancer Res., 1992, 52:2711s-2718s.*
Schartz et al., "Malignant effusions and immunogenic tumour-derived exosomes," Lancet, 360, 2002, pp. 295-305.
Bard et al., "Proteomic analysis of exosomes isolated from human malignant pleural effusions," Am J Respir Cell Mol Biol, 31, 2004, pp. 114-121.
Bartel, DP, "MicroRNAs: Genomics, biogenesis, mechanism, and function," Cell, 116, 2004, pp. 281-297.
Berek et al., "Biologic and immunologic therapies for ovarian cancer," J Clin Oncol, 21(s10), 2003, pp. 168-174.
Calin et al., "MicroRNA-cancer connection: the beginning of a new tale," Cancer Res, 66, 2006a, pp. 7390-7394.
Calin et al., "MicroRNA signatures in human cancers," Nature Rev Cancer, 6, 2006b, pp. 857-866.
Choi et al., "Proteomic analysis of microvesicles derived from human colorectal cancer cells," J Proteome Res, 6, 2007, pp. 4646-4655.
Cummins et al., "Implications of micro-RNA profiling for cancer diagnosis," Oncogene, 25, 2006, pp. 6220-6227.
De Cecco et al., "Gene expression profiling of advanced ovarian cancer: Characterisization of a molecular signature involving fibroblast growth factor 2," Oncogene, 23, 2004, pp. 8171-8183.
Esquela-Kerscher et al., "Oncomirs—microRNAs with a role in cancer," Nature Rev Cancer, 6, 2006, pp. 259-269.
Gaur et al., "Characterization of MicroRNA Expression Levels and Their Biological Correlates in Human Cancer Cell Lines," Cancer Res, 67:(6), 2007, pp. 2456-2468.
Iorio et al., "MicroRNA signatures in human ovarian cancer," Cancer Res, 67, 2007, pp. 8699-8707.
Iorio et al., "MicroRNA Gene Expression Deregulation in Human Breast Cancer," Cancer Res, 65:(16), 2005, pp. 7065-7070.
Escola et al., "Selective enrichment of tetraspan proteins on the internal vesicles of multivesicular endosomes and on exosomes secreted by human B-lymphocytes," J Biol Chem, 273, 1998, pp. 20121-20127.
Koga et al., "Purification, characterization and biological significance of tumor-derived exosomes," Anticancer Res, 25, 2005, pp. 3703-3707.
Lu et al., "MicroRNA expression profiles classify human cancers," Nature, 435, 2005, pp. 834-838.
Mears et al., "Proteomic analysis of melanoma-derived exosomes by two-dimensional polyacrylamide gel electrophoresis and mass spectrometry," Proteomics, 4, 2004, pp. 4019-4031.
Menon et al., "Recent developments in ovarian cancer screening," Curr Opin Obstet Gynecol, 12, 2000, pp. 39-42.

(Continued)

*Primary Examiner* — Jon E Angell
(74) *Attorney, Agent, or Firm* — Stites & Harbison, PLLC; Mandy Wilson Decker

(57) ABSTRACT

The presently disclosed subject matter provides methods of diagnosis of cancer or adverse pregnancy outcomes in a subject by measuring amounts of one or more microRNAs present in cancer-derived exosomes isolated from a biological sample from the subject.

24 Claims, 9 Drawing Sheets

OTHER PUBLICATIONS

Miska, EA., "How microRNAs control cell division, differentiation, and death," Curr Opi Genet Dev, 5, 2005, pp. 563-568.

Olver et al., "Proteomic analysis of secreted exosomes," Subcell Biochem., 43, 2007, pp. 99-131.

Paul et al., "MicroRNAs modulate the chemosensitivity of tumor cells," Mol Cancer Therap, 7, 2008, pp. 1-9.

Raposo et al., "Accumulation of major histocompatibility complex class II molecules in mast cell secretory granules and their release upon degranulation," Mol Biol Cell, 8, 1997, pp. 2631-2645.

Ratajczak et al., "Embryonic stem cell-derived microvesicles reprogram hematopoietic progenitors: Evidence for horizontal transfer of mRNA and protein delivery," Leukemia, 20, 2006, pp. 847-856.

Ratajczak et al., "Membrane-derived microvesicles: important and underappreciated mediators of cell-to-cell communication," Leukemia, 20, 2006, pp. 1487-1495.

Sabapatha et al., "Specific isolation of placental-derived exosomes from the circulation of pregnant women and their immunoregulatory consequences," Am J. Reprod Immunol, 56, 2006, pp. 345-355.

Sankaranarayanan, et al., "Worldwide burden of gynaecological cancer: the size of the problem," Best Pract Res Clin Obstet & Gynaecol, 20, 2006, pp. 207-225.

Seligson et al., "Epithelial Cell Adhesion Molecule (KSA) Expression: Pathobiology and Its Role as an Independent Predictor of Survival in Renal Cell Carcinoma," Clinical Cancer Research, vol. 10, 2004, pp. 2659-2669.

Taylor et al., "Binding of specific peroxidise-labeled antibody to placental-type alkaline phosphatise on tumor-derived membrane fragments," Cancer Res, 40, 1980, pp. 4964-4969.

Taylor et al., "Isolation of plasma membrane fragments from cultured murine melanoma cells," Biochem Biophys Res Comm, 113, 1983, pp. 470-476.

Taylor et al., "Shedding of plasma membrane fragments: Neoplastic and developmental importance," Developmental Biology, (M. Steinberg, ed.), vol. 3, 1986, pp. 33-57.

Taylor et al., "Neoplastic and developmental importance of plasma membrane vesicles," Amer. Zool., 26, 1987, pp. 411-415.

Taylor et al., "Shed membrane fragment-associated markers for endometrial and ovarian cancers," Gynecol Oncol, 84, 2002, pp. 443-448.

Taylor et al., "Tumour-derived exosomes and their role in cancer-associated T-cell signalling defects," Brit J Cancer, 92, 2005, pp. 305-311.

Taylor et al., "Pregnancy-linked suppression of TcR signaling pathways by a circulating factor absent in recurrent spontaneous pregnancy loss," Molecular Immunology, 43, 2006, pp. 1872-1880.

Taylor et al., "Pregnancy-Associated Exosomes and Their Modulation of T Cell Signaling," The Journal of Immunology, 176, 2006, pp. 1534-1542.

Valadi et al., "Exosome-mediated transfer of mRNAs and microRNAs is a novel mechanism of genetic exchange between cells," Nature Cell. Biol., 9, 2007, pp. 652-659.

Valenti et al., "Human tumor-released microvesicles promote the differentiation of myeloid cells with transforming growth factor-beta-mediated suppressive activity on T lymphocytes," Cancer Res, 66, 2006, pp. 9290-9298.

Yang et al., "MicroRNA expression profiling in human ovarian cancer: miR-214 induces cell survival and cisplatin resistance by targeting PTEN," Cancer Res, 68, 2008, pp. 425-433.

Yu et al., "The Regulation of Exosome Secretion: a Novel Function of the p53 Protein," Cancer Res, 66:(9), 2006, pp. 4795-4801.

Zhang et al., "microRNAs as oncogenes and tumor suppressors," Developmental Biology, 302, 2007, pp. 1-12.

Zhang et al., "microRNAs exhibit high frequency genomic alterations in human cancer," Proc Natl Acad Sci USA, 103, 2006, pp. 9136-9141.

SMETS et al., "Novel Biomarkers in Preeclampsia," Clinica Chimica Acta, 2006, vol. 364 (1-2), pp. 22-32.

EPO, Extended European Search Report for corresponding European Patent Application No. EP 08796656.0, Jan. 20, 2011, The Hague, NL.

Taylor et al., "Identification of antigenic components recognized by membrane-bound antibodies from ovarian cancer patients," American Journal of Reproductive Immunology, vol. 6, No. 4, Dec. 1, 1984, pp. 179-184, Munksgaard International Publishers, Copenhagen, DK.

Palacio et al., Anti-endometrial autoantibodies in women with a diagnosis of infertility, American Journal of Reproductive Immunology, vol. 38, Nr. 2, Aug. 1997, pp. 100-105.

Draghici Sorin et al., "Epitomics: Serum Screening for the Early Detection of Cancer on Microarrays Using Complex Panels of Tumor Antigens," Expert Review of Molecular Diagnostics, vol. 5, No. 5, 2005, pp. 735-743.

Taylor et al., "Shed Membrane Fragment-Associated Markers for Endometrial and Ovarian Cancers," Gynecologic Oncology, vol. 84, No. 3, 2002, pp. 443-448.

Taylor et al., "Tumour-derived Exosomes and Their Role in Cancer-Associated T-cell Signalling Defects," British Journal of Cancer, vol. 92, No. 2, 2005, pp. 305-311.

Taylor et al., "Pregnancy-Associated Exosomes and Their Modulation of T Cell Signaling," Journal of Immunology, American Association of Immunologists, US, vol. 176, No. 3, 2006, pp. 1534-1542.

Taylor et al., "Patient-Derived Tumor-Reactive Antibodies as Diagnostic Markers for Ovarian Cancer," Gynecologic Oncology, vol. 115, No. 1, 2009, pp. 112-120, Academic Press, London, GB.

Bohler et al., "Endometriosis Markers: 1-20 Immunologic Alterations as Diagnostic Indicators for Endometriosis," Reproductive Sciences, vol. 14(6), 2007, pp. 595-604, Sage Publications, Inc., US.

Taylor et al., "Characterization of Humoral Responses of Ovarian Cancer Patients: Antibody Subclasses and Antigenic Components," Gynecologic Oncology, vol. 116(2), 2010, pp. 213-221, Academic Press, London, GB.

EPO, Supplementary European Search Report for corresponding European Patent Application No. EP 08728418, completed May 20, 2010, The Hague, NL.

Taylor, et al., "Neoplastic and Developmental Importance of Shed Plasma Membrane Fragments," Amer. Zool. 1986, 26, pp. 511-514.

Kahlil, A., "Biomarker discovery: A proteomic approach for brain cancer profiling", Cancer Sci., 2007, 98(2), pp. 201-213.

Millimaggi, et al., "Tumor Vesicle-Associated CD147 Modulates the Angiogenic Capability of Endothelial Cells 1", Neoplasia, 2007, 9(4), pp. 349-357.

Piccin et al., "Circulating microparticles: pathophysiology and clinical implications", Elsevier Health, 2007, 21, pp. 157-171.

Schiera et al., "Neurons produce FGF2 and VEGF and secrete them at least in part by shedding extracellular vesicles", J. Cell Mol. Med., 2007, 11(6), pp. 1384-1394.

Andre, et al., "Exosomes for cancer immunotherapy," Annals of Oncology, 2004, 15 (Supplement 4): iv141-iv144; available at http://annonc.oxfordjournals.org, accessed Dec. 22, 2011.

Andre, et al., "Tumor-derived exosomes: a new source of tumor rejection antigens," Vaccine 20, 2002: A28-A31; available at www.elsevier.com/locate/vaccine.

Bard, et al., "Proteomic analysis of exosomes isolated from human malignant pleural effusions," Am. J. Respir. Cell Mol. Biol., 2004, vol. 31, pp. 114-121.

Caby, et al., "Exosomal-like vesicles are present in human blood plasma," International Immunology, 2005, vol. 17, No. 7, pp. 879-887.

Ceccarini, et al., "Biochemical and NMR studies on structure and release conditions of RNA-containing vesicles shed by human colon adenocarcinoma cells," Int. J. Cancer, 1989, vol. 44, pp. 714-721.

Clayton, et al., "Analysis of antigen presenting cell derived exosomes, based on immune-magnetic isolation and flow cytometry," Journal of Immunological Methods, 2001, vol. 247, pp. 163-174.

Dolo, et al., "Membrane vesicles shed into the extracellular medium by human breast carcinoma cells carry tumor-associated surface antigens," Clin. Exp. Metastasis, 1995, vol. 13, pp. 277-286.

Fevrier, et al., "Exosomes: endosomal-derived vesicles shipping extracellular messages," Current Opinion in Cell Biology, 2004, vol. 16, pp. 415-421.

Gassart, et al., "Lipid raft-associated protein sorting in exosomes," Blood, Dec. 15, 2003, vol. 102, No. 13, pp. 4336-4344; available at bloodjournal.hematologylibrary.org, accessed Dec. 17, 2011.

International search report dated Jan. 24, 2011 for PCT Application No. US10/58461.

Lamparski, et al., "Production and characterization of clinical grade exosomes derived from dendritic cells," Journal of Immunological Methods, 2002, vol. 270, pp. 211-226.

Monleon, et al., "Differential secretion of fas ligand—or APO2 ligand/TNF-related apoptosis-inducing ligand-carrying microvesicles during activation-induced death of human t cells," The Journal of Immunology, 2001, vol. 167, pp. 6736-6744.

Pang, et al., "MicroRNAs and prostate cancer," Acta Biochim Biophys Sin, 2010, vol. 42(6), pp. 363-369.

Thery, et al., "Exosomes: composition, biogenesis and function, Nature Reviews," Immunology, Aug. 2002, vol. 2, pp. 569-579.

Trubey, et al., "Quantitation of HLA class II protein incorporated into human immunodeficiency type 1 virions purified by anti-CD45 immunoaffinity depletion of microvesicles," Journal of Virology, Dec. 2003, pp. 12699-12709; available at http://jvi.asm.org, accessed Dec. 17, 2011.

Rosell et al., "Circulating MicroRNA Signatures of Tumor-Derived Exosomes for Early Diagnosis of Non- Small-Cell Lung Cancer," Clin Lung Canc, 2009, vol. 10, pp. 8-9.

Shih et al., "Exosomal microRNAs step into the biomarker arena," Gyn Onc, 2008, vol. 110, pp. 1-2.

Michael et al., "Exosomes from Human Saliva as a Source of microRNA Biomarkers," Oral Dis., Jan. 2010 vol. 16(1), pp. 34-38.

Chen et al., "Microfluidic isolation and transcriptome analysis of serum microvesicles," Lab Chip, 2010, vol. 10, pp. 505-511.

Keller et al., "Body fluid derived exosomes as a novel template for clinical diagnostics," Journal of Translational Medicine, 2011, vol. 9:86, pp. 1-23.

\* cited by examiner

CANCER-DERIVED MICROVESICLE-ASSOCIATED MICRORNA AS A DIAGNOSTIC MARKER

RELATED APPLICATIONS

This application claims priority from U.S. Provisional Application Ser. Nos. 60/951,812 filed on Jul. 25, 2007, and 61/050,438 filed on May 5, 2008, the entire disclosures of which are incorporated herein by this reference.

TECHNICAL FIELD

The presently disclosed subject matter relates to methods for diagnosis and prognosis of cancer and adverse pregnancy outcomes. In particular, the presently-disclosed subject matter relates to diagnostic and prognostic methods based on determining amounts of one or more exosome-derived microRNAs correlated with cancer or adverse pregnancy outcomes in a biological sample from a subject.

BACKGROUND

The identification of cancer biomarkers suitable for the early detection and diagnosis of cancer holds great promise to improve the clinical outcome of subjects. It is especially important for subjects presenting with vague or no symptoms or with tumors that are relatively inaccessible to physical examination. Despite considerable effort directed at early detection, few reliable and cost-effective screening tests have been developed that can diagnose cancer at an early stage.

As one example, ovarian cancer remains the sixth most common cancer in women worldwide, causing approximately 125,000 deaths annually (Sankaranarayanan & Ferlay, 2006). Most women with ovarian cancer are diagnosed at an advanced stage, with 75% diagnosed with extra-ovarian disease (Berek et al., 2003). In comparison with other cancers associated with women, 73% of endometrial cancers, 55% of breast cancers and 50% of cervical cancers are diagnosed with Stage I disease (Menon & Jacobs, 2000). While the 5-year survival of patients with Stage I ovarian cancer exceeds 90%, only 21% of advanced-stage ovarian cancer patients survive 5 years after initial diagnosis (Berek et al., 2003). Since long-term survival has not changed significantly in the past few decades, the best prospects for further improvement in ovarian cancer survival reside in early diagnosis (Menon & Jacobs, 2000).

The only biomarker currently approved for ovarian cancer detection is CA125 and its quantitation by ELISA has been the "gold standard" for detection of ovarian cancer since its introduction in 1983. Assessment of CA125 is typically used in disease management, both for disease detection as well as monitoring for disease recurrence; however, the use of CA125 is limited with regard to early stage cancer detection (sensitivity from 50-60%). CA125 quantitation is only approved for and consistently proven for remission monitoring. CA125 is neither sensitive nor specific for de novo ovarian cancer detection, since it is elevated in >50% of women with stage I disease, although it is elevated in more than 80% of patients with advanced stage ovarian cancer. CA125 has poor specificity, which is shown by its elevation in association with benign and malignant breast and colon disease, peritoneal irritants, and benign gynecologic diseases, among others.

New strategies that facilitate proteomic analysis by dramatically simplifying the pre-analytical sample separation and coupling with mass spectrometry (MS) have been introduced for biomarker discovery research. Surface-enhanced laser desorption/ionization time-of-flight mass spectrometry (SELDI-TOF-MS) has received much attention for its use in resolving proteins in biological specimens by binding to biochemically distinct protein chip arrays. In one technology, four serum proteins are examined by ELISA, while another technology uses mass spectrometry of seven specific serum components or general peptide patterns in patient serum to define the presence of cancer. SELDI-TOF-MS profiling has been successfully used to differentiate ovarian, breast, prostate, and liver cancer from controls.

SELDI-TOF-MS profiling of serum has been shown to be significantly better than the current standard serum biomarker CA125 at distinguishing patients with ovarian cancer from those with benign ovarian disease and from healthy controls. Studies have shown that the selection of a combination of multiple proteins resolved by SELDI-TOF-MS may have potential as a diagnostic approach. An effective screening test for ovarian cancer needs to achieve a high sensitivity and specificity and currently, different proteomic technologies as well as the computational analytic tools used to discern peaks generate different findings. These initial studies on SELDI-TOF-MS profiling insights are promising, and the concept is reproducible in a series of different backgrounds; however, translating this approach into a routine diagnostic test remains difficult.

It has been calculated that to be an effective screening test, an assay needs to achieve a minimum of 99.6% specificity. To achieve this level of specificity, multiple components of the tumor's characteristics will need to be incorporated into new diagnostic tests for effective detection because of the multifactorial nature of ovarian, as well as other cancers. A drawback of mass spectrometry techniques is that some samples of importance may be masked by more abundant proteins in the MS as well as in the analysis of the spectrometric output. Pre-purification by a number of techniques such as high-performance liquid chromatography and positive or negative selection through affinity binding can remove particular groups of proteins. The greatest challenge in most current mass spectrometry approaches is the dynamic range rather than sensitivity. While removal of prevalent proteins or peptides can greatly increase the informational content that can be acquired from particular samples, prevalent proteins such as albumin can function as carriers of protein subsets of diagnostic significance. Additional studies with larger samples sizes and careful blinding of the independent validation sets are needed before any consideration of application of this platform for screening for ovarian cancer or any other indication should be considered.

Thus, a need persists for the development of improved biomarkers in nearly all cancers and other disorders, including the increased risk for adverse pregnancy outcomes. Blood-based assays remain an attractive goal due to the availability and ease of sample collection. Earlier definitive diagnosis of cancer and increased risk for adverse pregnancy outcomes would facilitate earlier and potentially more effective treatment of patients. As such, there is an unmet need for new biomarkers that individually, or in combination with other biomarkers or diagnostic modalities, deliver the required sensitivity and specificity for early detection and prognosis of cancer and adverse pregnancy outcomes. In particular, simple tests for cancer biomarkers and adverse pregnancy outcomes performed on readily-accessible biological fluids are needed.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments of the presently-disclosed subject matter, a method for diagnosing a cancer in a subject is provided. In some embodiments, the method comprises providing a biological sample from a subject; isolating cancer-derived exosomes comprising microRNAs (miRNAs) from the biological sample; determining an amount of one or more of the miRNAs; and comparing the amount of the one or more miRNAs to one or more miRNA control levels. The subject is then diagnosed as having the cancer if there is a measurable difference in the amount of the one or more miRNAs from the cancer-derived exosomes as compared to the one or more miRNA control levels. In some embodiments, the method further comprises selecting a treatment or modifying a treatment for the cancer based on the amount of the one or more miRNAs determined.

In other embodiments of the presently-disclosed subject matter, a method for evaluating treatment efficacy and/or progression of a cancer in a subject is provided. In some embodiments, the method comprises providing a series of biological samples over a time period from a subject; isolating cancer-derived exosomes comprising miRNAs from the series of biological samples; determining an amount of one or more of the miRNAs in each of the biological samples from the series; and determining any measurable change in the amounts of the one or more miRNAs in each of the biological samples from the series to thereby evaluate treatment efficacy and/or progression of the cancer in the subject.

In still other embodiments of the presently-disclosed subject matter, a method for characterizing a cancer in a subject is provided. In some embodiments, the method comprises providing a biological sample from a subject; isolating cancer-derived exosomes comprising miRNAs from the biological sample; determining an amount of one or more of the miRNAs; and comparing the amount of the one or more miRNAs to one or more miRNA control levels. The cancer is then characterized based on a measurable difference in the amount of the one or more miRNAs from the cancer-derived exosomes as compared to the one or more miRNA control levels. In some embodiments, characterizing the cancer comprises determining a type, a grade, and/or a stage of the cancer. Further, in some embodiments, determining the amount of the one or more miRNAs comprises determining a total amount of the miRNA in the cancer-derived exosomes.

In some embodiments of these methods, the cancer is a cancer selected from the group consisting of ovarian cancer, cervical cancer, breast cancer, endometrial cancer, colon cancer, prostate cancer, lung cancer, melanoma, and pancreatic cancer.

Further, in some of these methods, isolating the cancer-derived exosomes further comprises using size exclusion chromatography to isolate the cancer-derived exosomes. In some embodiments, isolating the cancer-derived exosomes comprises centrifuging a chromatography fraction comprising the cancer-derived exosomes. The chromatography fraction can be in some embodiments a void volume fraction.

Still further, in some embodiments, the cancer-derived exosomes are separated from non-cancer-derived exosomes by immunosorbent capture using an anti-cancer antigen antibody, such as for example an anti-epithelial cell adhesion molecule (anti-EpCAM) antibody.

In some of these methods, determining the amount of the one or more miRNAs comprises labeling the one or more miRNAs, and in some embodiments, then capturing the one or more miRNAs with one or more polynucleotide probes that each selectively bind the one or more miRNAs. In other embodiments of these methods, determining the amount of the one or more miRNAs comprises using a real-time polymerase chain reaction to quantitate the amount of the one or more miRNAs. Further, in some embodiments of these methods, the miRNAs are one or more miRNAs set forth in Table 2, including for example one or more miRNAs selected from the group consisting of miR-21, miR-141, miR-200a, miR-200b, miR-200c, miR-203, miR-205, and miR-214.

In still other embodiments of the presently-disclosed subject matter, a method for diagnosing adverse pregnancy outcomes in a subject is provided. In some embodiments, the method comprises providing a biological sample from a subject; isolating exosomes comprising miRNAs from the biological sample; determining an amount of one or more of the miRNAs; and comparing the amount of the one or more miRNAs to one or more miRNA control levels. The subject is diagnosed with the adverse pregnancy outcome if there is a measurable difference in the amount of the one or more miRNAs from the exosomes as compared to the one or more miRNA control levels. In some embodiments, the adverse pregnancy outcome is a disorder selected from the group consisting of premature rupture of membranes, preeclampsia, preterm birth, intrauterine growth restriction, and recurrent pregnancy loss.

In some of the embodiments disclosed herein the subject is human. Further, In some of the embodiments disclosed herein the biological sample comprises milk, blood, serum, plasma, ascites, cyst fluid, pleural fluid, peritoneal fluid, cerebral spinal fluid, tears, urine, saliva, sputum, or combinations thereof.

Accordingly, it is an object of the presently disclosed subject matter to utilize exosome-associated miRNAs as diagnostic markers. This object is achieved in whole or in part by the presently disclosed subject matter.

An object of the presently disclosed subject matter having been stated hereinabove, and which is achieved in whole or in part by the presently disclosed subject matter, other objects and advantages will become evident to those of ordinary skill in the art after a study of the following description of the presently disclosed subject matter, figures, and non-limiting examples.

BRIEF DESCRIPTION OF THE FIGURES

(FIG. 7A) or after 7 to 28 days, stored at −70° C. (FIG. 7B). Tumor exosomes were isolated by MACS using anti-EpCAM.

DETAILED DESCRIPTION

Figure 1:
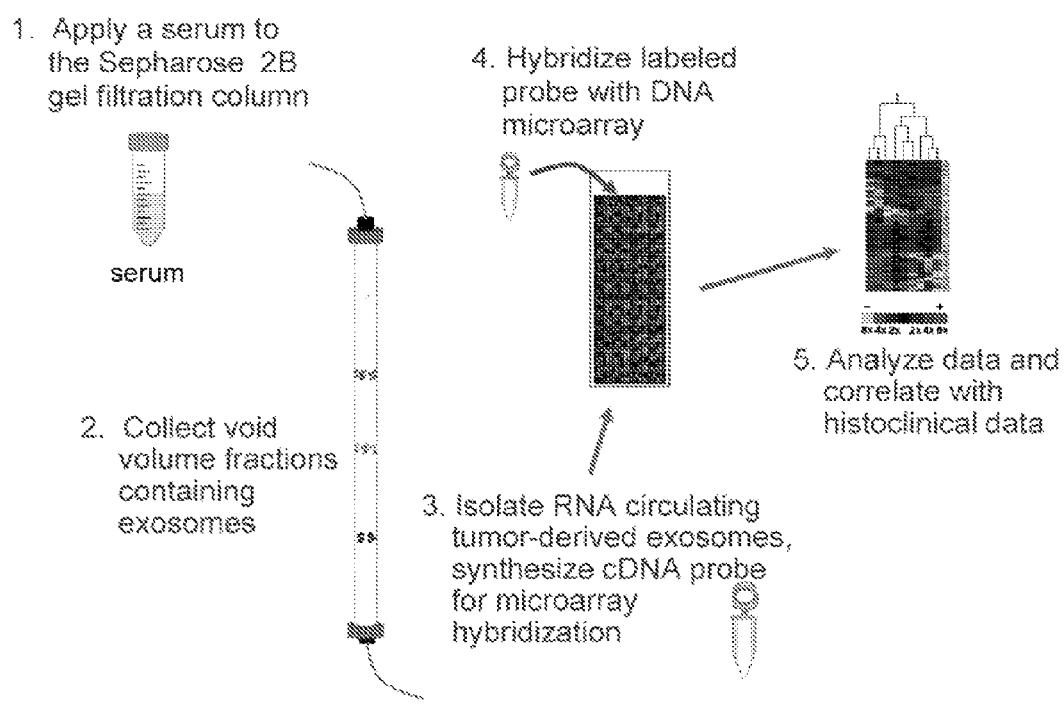
FIG. 1 is a schematic diagram showing exemplary methodology for chromatographically isolating cancer-derived exosomes and miRNA from the exosomes, determining amounts of the miRNA by microarray, and analyzing the data to determine if cancer is present in the subject tested.

The details of one or more embodiments of the presently disclosed subject matter are set forth in the accompanying description below. Other features, objects, and advantages of the presently disclosed subject matter will be apparent from the specification, Figures, and Claims. All publications, patent applications, patents, and other references noted herein are incorporated by reference in their entirety. In case of conflict, the present specification, including definitions, will control.

Unless defined otherwise, all technical and scientific terms used herein have the same meaning as commonly understood by one of ordinary skill in the art to which the presently disclosed subject matter belongs. Although any methods, devices, and materials similar or equivalent to those described herein can be used in the practice or testing of the presently disclosed subject matter, representative methods and materials are now described.

Following long-standing patent law convention, the terms "a", "an", and "the" refer to "one or more" when used in this application, including the claims. Thus, for example, reference to "a peptide" includes a plurality of such peptides, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

Over the last 5 years, expression profiling technologies have identified new biomarkers with diagnostic applications. One such biomarker group is a class of small non-coding RNAs, termed microRNAs (miRNAs) (Iorio et al. 2007; De Cecco et al., 2004; Calin & Croce, 2006). MicroRNAs, small (22-25 nucleotides in length) non-coding RNAs, suppress the translation of target mRNAs by binding to their 3' untranslated region (Esquela-Kerscher & Slack, 2006; Bartel, 2004). Post-transcriptional silencing of target genes by miRNA can occur either by cleavage of homologous mRNA or by specific inhibition of protein synthesis.

All tumors analyzed by miRNA profiling have exhibited significantly distinct miRNA signatures, compared with normal cells from the same tissue (Iorio et al. 2007; Calin & Croce, 2006a; Calin & Croce, 2006b). Lu et al. (2005) performed an analysis of leukemias and solid cancers and determined that miRNA-expression profiles could classify human cancers by developmental lineage and differentiation state. The expressions of individual miRNAs and specific miRNA signatures have now been linked to the diagnosis and prognosis of many human cancers.

Using tissue specimens, Iorio et al. (2007) demonstrated that, in comparison to normal ovary, specific miRNAs were aberrantly expressed in ovarian cancer, with miR-141, miR-200a, miR-200b, and miR-200c being the most significantly overexpressed. They further demonstrated the hypomethylation in ovarian tumors resulted in the up-modulation of miR-21, miR-203, and miR-205, compared with normal ovary. Two of these up-modulated miRNAs, miR-200a and miR-200c, were enhanced in all the three histologic types examined (serous, endometrioid, and clear cell), whereas miR-200b and miR-141 up-modulation was shared by endometrioid and serous histologic types. In general, the miRNA signatures obtained comparing different histologic types of ovarian cancers (serous, endometrioid, clear cell, and mixed) with the normal tissue were overlapping in most cases. Their analysis of ovarian tumors also demonstrated the absence of differentially expressed miRNAs in relation to tumor stage or grade, which could have resulted from their set of samples being primarily derived from advanced stage tumors.

Among the miRNAs most significantly up-modulated, miR-200a and miR-141 belong to the same family, miR-200b is localized on chromosome 1p36.33 in the same region as miR-200a and miR-200c is localized on chromosome 12p13.31 in the same region of miR-141 (Iorio et al. (2007)). This association would agree with the findings of Zhang et al. (2006) that proposed that the up-modulation of specific miR-NAs could be the amplification of the miRNA genes. Using high-resolution array-based comparative genomic hybridization, an aberrantly high proportion of loci containing miRNA genes exhibited DNA copy number alterations. In ovarian cancer, 37.1% of the genomic loci containing miRNA genes were associated with DNA copy number alterations (Zhang et al., 2006). In breast cancer and melanoma, an even greater proportion of these loci exhibit altered DNA copy numbers (72.8% and 85.9%, respectively) (Zhang et al., 2006). As a result, miRNA expression patterns, or signatures, appear to be more characteristic of the developmental origins of tumors than mRNA expression patterns and may be associated with diagnosis, staging, progression, prognosis, and response to treatment. However, as cancer diagnostic tools, prior to the presently-disclosed subject matter, the analyses of miRNA signatures have been limited to tissue biopsies.

A recently described characteristic of cancer cells is their ability to release or shed intact, vesicular portions of the plasma membrane (termed "exosomes" herein, and also known in the art as membrane fragments, membrane vesicles, or microvesicles). Disclosed herein are data surprisingly identifying for the first time miRNAs associated with exosomes originating from cancer cells (i.e., "cancer-derived exosomes"). The presently disclosed subject matter further discloses for the first time that miRNA isolated from cancer-derived exosomes exhibits expression levels in subjects suffering from cancer that differ (e.g., increased or decreased) from miRNA expression levels measured in subjects free of cancer (referred to herein as "miRNA control levels"). Further, the presently disclosed subject matter provides for the isolation of cancer-derived exosomes from readily-accessible biological fluids from a test subject. As such, the presently disclosed subject matter provides for the first time methods for diagnosis and prognosis of cancer based on the collection and measurement of cancer-derived exosome miRNA levels from readily-accessible biological samples, and without necessitating direct sampling of cancer cells.

"Exosomes" are microvesicles released from a variety of different cells, including cancer cells (i.e., "cancer-derived exosomes"). These small vesicles (50-100 nm in diameter) derive from large multivesicular endosomes and are secreted into the extracellular milieu. The precise mechanisms of exosome release/shedding remain unclear; however, this release is an energy-requiring phenomenon, modulated by extracellular signals. They appear to form by invagination and budding from the limiting membrane of late endosomes, resulting in vesicles that contain cytosol and that expose the extracellular domain of membrane-bound cellular proteins on their surface. Using electron microscopy, studies have shown fusion profiles of multivesicular endosomes with the plasma membrane, leading to the secretion of the internal vesicles into the extracellular environment. The rate of exosome release is significantly increased in most neoplastic cells and occurs continuously. Increased release of exosomes and their accumulation appear to be important in the malignant transformation process. In addition to cancer cells, the release of exosomes has also been demonstrated to be associated with cells of embryonic origin (such as the placenta) and activated lymphoid cells.

Although extracellular shedding of exosomes occurs in other types of cells, under specific physiological conditions, the accumulation of exosomes from non-neoplastic cells is rarely observed in vivo. In contrast, exosomes released by tumor cells accumulate in biologic fluids, including in sera, ascites, and pleural fluids. Exosome release and its accumulation appear to be important features of the malignant transformation. Shed cancer-derived exosomes do not mirror the general composition of the plasma membrane of the originating tumor cell, but represent 'micromaps,' with enhanced expression of tumor antigens.

The release of exosomes appears to be an important feature of intercellular communication. Since released exosomes express molecules with biologic activity (such as Fas ligand, PD-1, MICA/B, mdr1, MMPs, CD44, and autoreactive antigens), the ability of these microvesicles to modulate lymphocyte and monocyte functions have been analyzed in several models. It has been theorized that these released exosomes modulate lymphocyte functions by mimicking "activation induced cell death" (AICD). Lymphoid cells appear to release exosomes following activation and these appear to play an essential role in immunoregulation, by preventing excessive immune responses and the development of autoimmunity. It has been postulated that exosome release by tumor cells is a re-expression of the fetal cell exosomes and that both constitute pathways to circumvent immunosurveillance.

MicroRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression.

There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

MicroRNAs function by engaging in base pairing (perfect or imperfect) with specific sequences in their target genes' messages (mRNA). The miRNA degrades or represses translation of the mRNA, causing the target genes' expression to be post-transcriptionally down-regulated, repressed, or silenced. In animals, miRNAs do not necessarily have perfect homologies to their target sites, and partial homologies lead to translational repression, whereas in plants, where miRNAs tend to show complete homologies to the target sites, degradation of the message (mRNA) prevails.

MicroRNAs are widely distributed in the genome, dominate gene regulation, and actively participate in many physiological and pathological processes. For example, the regulatory modality of certain miRNAs is found to control cell proliferation, differentiation, and apoptosis; and abnormal miRNA profiles are associated with oncogenesis. Additionally, it is suggested that viral infection causes an increase in miRNAs targeted to silence "pro-cell survival" genes, and a decrease in miRNAs repressing genes associated with apoptosis (programmed cell death), thus tilting the balance towards gaining apoptosis signaling.

Thousands of mRNA are under this selection pressure by hundreds of miRNA species identified so far. This selection process is instrumental in dampening specific groups of gene expressions which, for example, may no longer be needed, to allow cells to channel their physiological program direction to a new pathway of gene expression. The miRNA-dependent dampening of target groups of gene expression is a robust and rapid regulation to allow cells to depart from an old, and transition to a new, program. A typical example of this is demonstrated during embryonic development, when a particular group of cells is directed to become unique specialized cell types such as neurons, cardiomyocytes, muscle, etc.

It is thought that expression levels of roughly a third of human genes are regulated by miRNAs, and that the miRNA regulation of unique gene expressions is linked to the particular signaling pathway for each specific cell type. For example, the apoptosis signaling pathway may be dictated by a group of miRNAs targeted to destabilize pro-survival gene messages, allowing alternative pro-apoptosis genes to gain dominance and thus activate the death program. Another example is the control of cancer growth; a recent discovery has shown that miRNAs may also be essential in preventing cells from becoming neoplastic. For example, two oncogenes, cMyc and cRas, are found to share control by one miRNA species, whose expression is down-regulated in cancer. In other words, lack of this miRNA allows the unchecked expression of cMyc and cRas, thus permitting these two genes to become abundantly present in cancer cells, allowing them to acquire uncontrolled cell proliferating ability, and set the stage for neoplastic growth. Additionally, it has been reported that a miRNA mutation is responsible for a phenotype of muscularity in sheep of Belgian origin, suggesting that mutations associated with genetic disorders could be found in miRNAs, where no evidence of mutations have been found in promoter regions, coding areas, and slicing sites.

It is possible that a coordinated orchestration of multiple pathways serves to control a particular cellular state, wherein certain molecular "hubs" may be involved, which are functionally manipulated by hierarchical orders and redundancy of molecular control. Indeed, dozens of miRNAs may operate to ensure that these "hubs" can exert either major or minor functions in cells, by simply repressing the expression of either themselves or their functional opponents. Thus, one gene product may function as a major "hub" for one signaling pathway in one type of cell, and in another cell type, it may be a minor "hub", or may not be used at all. MicroRNA control of "hub" gene expressions may then be an expedient mechanism to provide such versatility for various molecules to serve as either major or minor "hubs", or not at all, for different types of cellular operational modalities.

Given the role of miRNAs in gene regulation, and in many physiological and pathological processes, information about their interactive modes and their expression patterns is desirable to obtain. Systems and methods of quantitating and identifying which groups of putative miRNAs are in operation in a particular cell type, or in association with a particular process or condition of interest, can provide information useful for understanding how each cellular state evolves and is maintained, and how dysfunctional maintenance is abetted by improper decreases or increases of unique sets of miRNAs to regulate the expression of key genes. Such understanding can prove useful in the diagnosis and characterization of a number of disorders, including cancer and adverse pregnancy outcomes.

As potential clinical diagnostic tools miRNAs have been shown to be important and accurate determinants for many if not all cancers. Increasing evidence shows that expression of miRNA genes is deregulated in human cancer. The expression of miRNAs is highly specific for tissues and developmental stages and has allowed recently for molecular classification of tumors. To date, all tumors analyzed by miRNA profiling have shown significantly different miRNA profiles compared with normal cells from the same tissue. Flow-cytometric miRNA profiling demonstrated that miRNA-expression profiles classify human cancers according to the developmental lineage and differentiation state of the tumors. Specific over- or underexpression has been shown to correlate with particular tumor types. MicroRNA overexpression could result in down-regulation of tumor suppressor genes, whereas their underexpression could lead to oncogene up-regulation. Using large-scale microarray analysis, cancer cells showed distinct miRNA profiles compared with normal cells with 36 of the 228 miRNA genes overexpressed and 21 downregulated in cancer cells versus normal cells. Hierarchical clustering analyses showed that this miRNA signature enabled the tumor samples to be grouped on the basis of their tissue of origin. Genome-wide profiling studies have been performed on various cancer types, including CLL, breast cancer, glioblastoma, thyroid papillary carcinoma, hepatocellular carcinoma, ovarian cancer, colon cancer, and endocrine pancreatic tumors. In a study of 104 matched pairs of primary cancerous and non-cancerous ovarian tissue, 43 differentially expressed miRNAs were observed; 28 were downregulated and 15 were overexpressed in tumors.

Statistical analyses of microarray data obtained by two different methods, significance analysis of microarrays (SAM) and prediction analysis of microarrays (PAM) from six solid tumors (ovarian, breast, colon, gastric and prostate carcinomas and endocrine pancreatic tumors), demonstrated a common signature composed of 21 miRNAs differentially expressed in at least three tumor types. At the top of the list were miR-21, which was overexpressed in six types of cancer cells, and miR-17-5p and miR-191, which were overexpressed in five. As the embryological origin of the analyzed tumors was different, the significance of such findings could be that these common miRNAs participate in fundamental signaling pathways altered in many types of tumor. Supporting the function of these genes in tumorigenesis, it was found that the predicted targets for the differentially expressed miRNAs are significantly enriched for those that target known tumor suppressors and oncogenes. Furthermore, miR-21, the only miRNA overexpressed in all six types of cancer analyzed was shown to directly target the tumor suppressor PTEN, which encodes a phosphatase inhibiting growth and/or survival pathways. The function of PTEN is altered in advanced tumors of various types, including breast, ovarian, gastric and prostate.

In some embodiments of the presently disclosed subject matter, a method for diagnosing a cancer in a subject is provided. In some embodiments, the method comprises providing a biological sample from a subject; isolating cancer-derived exosomes comprising miRNAs from the biological sample; determining an amount of one or more of the miRNAs; and comparing the amount of the one or more miRNAs to one or more miRNA control levels. The subject can then be diagnosed as having the cancer if there is a measurable difference in the amount of the one or more miRNAs from the cancer-derived exosomes in the sample as compared to the one or more control levels. A non-limiting list of exemplary miRNAs that can be measured are provided in Tables 1 and 2. In some embodiments, the miRNAs measured are selected from the miRNAs listed in Table 2, and in some particular embodiments, the miRNAs measured are miRNAs selected from the group consisting of miR-21, miR-141, miR-200a, miR-200b, miR-200c, miR-203, miR-205, and miR-214.

The term "cancer" refers to all types of cancer or neoplasm or malignant tumors found in animals, including leukemias, carcinomas and sarcomas. Examples of cancers are cancer of the brain, bladder, breast, cervix, colon, head and neck, kidney, lung, non-small cell lung, melanoma, mesothelioma, ovary, pancreas, prostate, sarcoma, stomach, and uterus.

By "leukemia" is meant broadly to include progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, a leukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

In some particular embodiments, the cancer is a cancer selected from the group consisting of ovarian cancer, cervical cancer, breast cancer, endometrial cancer, colon cancer, prostate cancer, lung cancer, melanoma, and pancreatic cancer.

The term "biological sample" as used herein refers to a sample that comprises a biomolecule and/or is derived from a subject. Representative biomolecules include, but are not limited to total DNA, RNA, miRNA, mRNA, and polypeptides. The biological sample can be utilized for the detection of the presence and/or expression level of a miRNA of interest associated with cancer-derived exosomes. Any cell, group of cells, cell fragment, or cell product can be used with the methods of the presently claimed subject matter, although biological fluids and organs that would be predicted to contain cancer-derived exosomes exhibiting differential expression of miRNAs as compared to normal controls are best suited. In some embodiments, the biological sample is a relatively easily obtained biological sample, such as for example blood or a component thereof. In some embodiments, the biological sample comprises milk, blood, serum, plasma, ascites, cyst fluid, pleural fluid, peritoneal fluid, cerebral spinal fluid, tears, urine, saliva, sputum, or combinations thereof.

In some embodiments, size exclusion chromatography can be utilized to isolate the cancer-derived exosomes. See, e.g., FIGS. 1 and 2. Size exclusion chromatography techniques are known in the art. Exemplary, non-limiting techniques are provided in the present Examples. In some embodiments, a void volume fraction is isolated and comprises the exosomes of interest. Further, in some embodiments, the cancer-derived exosomes can be further isolated after chromatographic separation by centrifugation techniques (of one or more chromatography fractions), as is generally known in the art. In some embodiments, for example, density gradient centrifugation can be utilized to further isolate the exosomes. Still further, in some embodiments, it can be desirable to further separate the cancer-derived isolated exosomes from exosomes of other origin. For example, the cancer-derived exosomes can be separated from non-cancer-derived exosomes by immunosorbent capture using an anti-cancer antigen antibody. See, e.g., FIG. 8. Exemplary anti-cancer antigen antibodies include, but are not limited to, anti-epithelial cell adhesion molecule (anti-EpCAM) antibodies, utilized as, for example, set forth in the present Examples.

The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a biomarker (e.g., an miRNA expression level), the amount (including presence or absence) of which is indicative of the presence, severity, or absence of the condition.

Along with diagnosis, clinical cancer prognosis is also an area of great concern and interest. It is important to know the aggressiveness of the cancer cells and the likelihood of tumor recurrence in order to plan the most effective therapy. Some cancers, for example, are managed by several alternative strategies. In some cases local-regional and systemic radiation therapy is utilized while in other cases surgical intervention and/or chemotherapy are employed. Current treatment decisions for individual cancer subjects can be based on (1) the number of lymph nodes involved with disease, (2) cancer marker(s) status, (3) the size of the primary tumor, and (4) stage of disease at diagnosis. However, even with these factors, accurate prediction of the course of disease for all cancer subjects is not possible. If a more accurate prognosis can be made, appropriate therapy, and in some instances less severe therapy, for the patient can be chosen. Measurement of cancer-derived exosome miRNA levels disclosed herein can be useful in order to categorize subjects according to advancement of cancer who will benefit from particular therapies and differentiate from other subjects where alternative or additional therapies can be more appropriate. As such, in some embodiments of the presently disclosed subject matter, a method for characterizing a cancer in a subject is provided. In some embodiments, the method comprises providing a biological sample from a subject; isolating cancer-derived exosomes comprising micro-RNAs (miRNAs) from the biological sample; determining an amount of one or more of the miRNAs; and comparing the amount of the one or more miRNAs to one or more miRNA control levels. In such embodiments, the cancer can be characterized based on a measurable difference in the amount of the one or more miRNAs from the cancer-derived exosomes as compared to the one or more miRNA control levels. In some embodiments, characterizing the cancer comprises determining a type, a grade, and/or a stage of the cancer.

"Making a diagnosis" or "diagnosing", as used herein, is further inclusive of making a prognosis, which can provide for predicting a clinical outcome (with or without medical treatment), selecting an appropriate treatment (or whether treatment would be effective), or monitoring a current treatment and potentially changing the treatment, based on the measure of cancer-derived exosomal diagnostic miRNA levels. Further, in some embodiments of the presently disclosed subject matter, multiple determination of amounts of one or more miRNAs over time can be made to facilitate diagnosis (including prognosis), evaluating treatment efficacy, and/or progression of a cancer. A temporal change in one or more cancer-derived exosomal miRNA levels (i.e., miRNA amounts in a biological sample) can be used to predict a clinical outcome, monitor the progression of the cancer, and/or efficacy of administered cancer therapies. In such an embodiment for example, one could observe a decrease in the amount of particular miRNAs in a biological sample over time during the course of a therapy, thereby indicating effectiveness of treatment.

The presently disclosed subject matter further provides in some embodiments a method for evaluating treatment efficacy and/or progression of a cancer in a subject. In some embodiments, the method comprises providing a series of biological samples over a time period from the subject; isolating cancer-derived exosomes comprising miRNAs from the series of biological samples; determining an amount of one or more of the miRNAs in each of the biological samples from the series; and determining any measurable change in the amounts of the one or more miRNAs in each of the biological samples from the series to thereby evaluate treatment efficacy and/or progression of the cancer in the subject. Any changes in the amounts of measured miRNAs over the time period can be used to predict clinical outcome, determine whether to initiate or continue the therapy for the cancer, and whether a current therapy is effectively treating the cancer. For example, a first time point can be selected prior to initiation of a treatment and a second time point can be selected at some time after initiation of the treatment. miRNA levels can be measured in each of the samples taken from different time points and qualitative and/or quantitative differences noted. A change in the amounts of one or more of the measured miRNA levels from the first and second samples can be correlated with prognosis, determining treatment efficacy, and/or progression of the disease in the subject.

The terms "correlated" and "correlating," as used herein in reference to the use of diagnostic and prognostic miRNA levels associated with cancer, refers to comparing the presence or quantity of the miRNA levels in a subject to its presence or quantity in subjects known to suffer from a cancer, or in subjects known to be free of the cancer, i.e. "normal subjects" or "control subjects". For example, a level of one or more miRNAs in a biological sample can be compared to a miRNA level for each of the specific miRNAs tested and determined to be correlated with a cancer. The sample's one or more miRNA levels is said to have been correlated with a diagnosis; that is, the skilled artisan can use the miRNA level(s) to determine whether the subject suffers from the cancer and respond accordingly. Alternatively, the sample's miRNA level(s) can be compared to control miRNA level(s) known to be associated with a good outcome (e.g., the absence of cancer), such as an average level found in a population of normal subjects.

In certain embodiments, a diagnostic or prognostic miRNA level is correlated to a cancer by merely its presence or absence. In other embodiments, a threshold level of a diagnostic or prognostic miRNA level can be established, and the level of the miRNA in a subject sample can simply be compared to the threshold level.

As noted, in some embodiments, multiple determinations of one or more diagnostic or prognostic miRNA levels can be made, and a temporal change in the levels can be used to determine a diagnosis or prognosis. For example, specific miRNA level(s) can be determined at an initial time, and again at a second time. In such embodiments, an increase in the miRNA level(s) from the initial time to the second time can be diagnostic of the cancer, or a given prognosis. Likewise, a decrease in the miRNA level(s) from the initial time to the second time can be indicative of the cancer, or a given prognosis. Furthermore, the degree of change of one or more miRNA level(s) can be related to the severity of the cancer and/or timeline of disease progression and future adverse events.

The skilled artisan will understand that, while in certain embodiments comparative measurements can be made of the same miRNA level(s) at multiple time points, one can also measure given miRNA level(s) at one time point, and second miRNA level(s) at a second time point, and a comparison of these levels can provide diagnostic information.

The phrase "determining the prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of a biomarker. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not expressing the miRNA level(s) or expressing miRNA level(s) at a reduced level), the chance of a given outcome (e.g., suffering from cancer) may be very low (e.g., <1%), or even absent. In contrast, in individuals exhibiting the condition (e.g., expressing the miRNA level(s) or expressing miRNA level(s) at a level greatly increased over a control level), the chance of a given outcome (e.g., suffering from a form/stage of cancer) may be high. In certain embodiments, a prognosis is about a 5% chance of a given expected outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, miRNA level(s) (e.g., quantity of one or more miRNAs in a sample) of greater or less than a control level in some embodiments can signal that a subject is more likely to suffer from a cancer than subjects with a level less than or equal to the control level, as determined by a level of statistical significance. Additionally, a change in miRNA level(s) from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the level of a prognostic or diagnostic miRNA level(s) can be established, and the degree of change in the level of the indicator in a biological sample can simply be compared to the threshold degree of change in the level. A preferred threshold change in the level for miRNA level(s) of the presently disclosed subject matter is about 5%, about 10%, about 15%, about 20%, about 25%, about 30%, about 50%, about 60%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

The identity and relative quantity of miRNAs in a sample can be used to provide miRNA profiles for a particular sample. An miRNA profile for a sample includes information about the identities of miRNAs contained in the sample, quantitative levels of miRNAs contained in the sample, and/or changes in quantitative levels of miRNAs relative to another sample. For example, an miRNA profile for a sample includes information about the identities, quantitative levels, and/or changes in quantitative levels of miRNAs associated with a particular cancer.

Further with respect to the diagnostic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

As noted hereinabove, the presently disclosed subject matter provides for the determination of the amount of cancer-derived exosomal miRNAs correlated with cancer within biological fluids of a subject, and in particular, from serological samples from a subject, such as for example blood. This provides the advantage of biological samples for testing that are easily acquired from the subject. The amount of one or more miRNAs of interest in the biologic sample can then be determined utilizing any of a number of methodologies generally known in the art and compared to miRNA control levels.

The "amount" of one or more miRNAs determined refers to a qualitative (e.g., present or not in the measured sample) and/or quantitative (e.g., how much is present) measurement of the one or more miRNAs. The "control level" is an amount (including the qualitative presence or absence) or range of amounts of one or more miRNAs found in a comparable biological sample in subjects not suffering from cancer. As one non-limiting example of calculating the control level, the amount of one or more miRNAs of interest present in a normal biological sample (e.g., blood) can be calculated and extrapolated for whole subjects.

Figure 8:
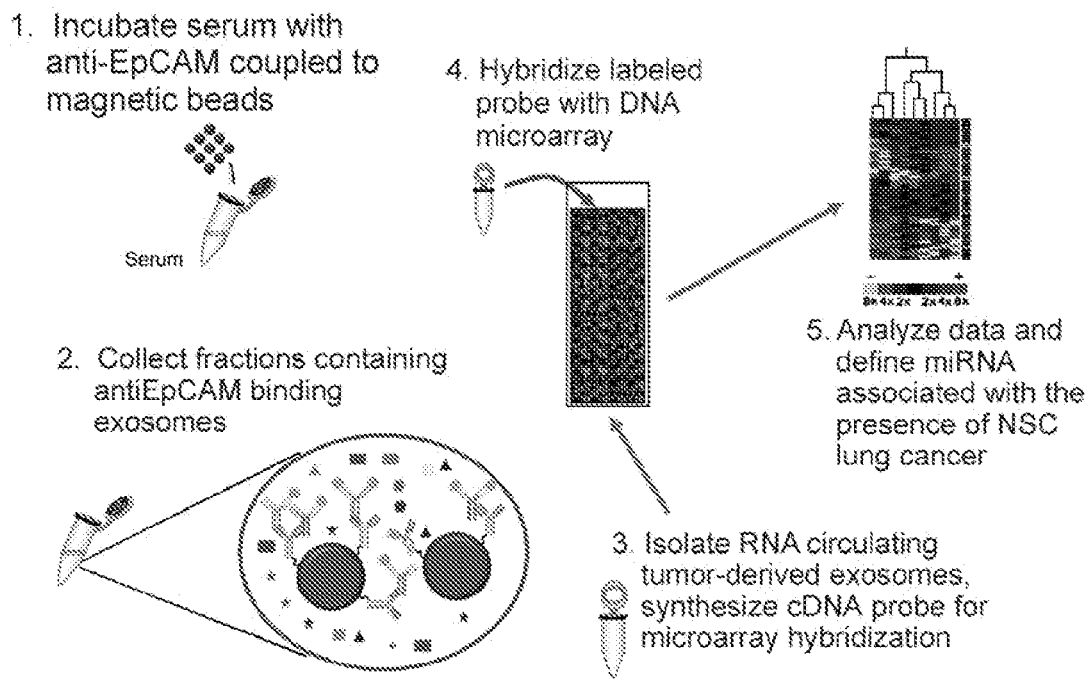
FIG. 8 is a schematic diagram showing exemplary methodology for isolating cancer-derived exosomes and miRNA from the exosomes, determining amounts of the miRNA by microarray, and analyzing the data to determine if cancer is present in the subject tested.

An exemplary methodology for measuring miRNA levels from exosomes in a biological sample is microarray technique, which is a powerful tool applied in gene expression studies. The technique provides many polynucleotides with known sequence information as probes to find and hybridize with the complementary strands in a sample to thereby capture the complementary strands by selective binding. FIGS. 1 and 8 provide flowcharts of exemplary protocols for isolating and measuring exosomal-derived miRNAs by microarray.

The term "selective binding" as used herein refers to a measure of the capacity of a probe to hybridize to a target polynucleotide with specificity. Thus, the probe comprises a polynucleotide sequence that is complementary, or essentially complementary, to at least a portion of the target polynucleotide sequence. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide. With regard to probes disclosed herein having binding affinity to miRNAs, the probe can be 100% complementary with the target polynucleotide sequence. However, the probe need not necessarily be completely complementary to the target polynucleotide along the entire length of the target polynucleotide so long as the probe can bind the target polynucleotide with specificity and capture it from the sample.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by the skilled artisan. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. Determining appropriate hybridization conditions to identify and/or isolate sequences containing high levels of homology is well known in the art. For the purposes of specifying conditions of high stringency, preferred conditions are a salt concentration of about 200 mM and a temperature of about 45° C.

Data mining work is completed by bioinformatics, including scanning chips, signal acquisition, image processing, normalization, statistic treatment and data comparison as well as pathway analysis. As such, microarray can profile hundreds and thousands of polynucleotides simultaneously with high throughput performance. Microarray profiling analysis of mRNA expression has successfully provided valuable data for gene expression studies in basic research. And the technique has been further put into practice in the pharmaceutical industry and in clinical diagnosis. With increasing amounts of miRNA data becoming available, and with accumulating evidence of the importance of miRNA in gene regulation, microarray becomes a useful technique for high through-put miRNA studies.

The analysis of miRNA correlated with cancer can be carried out separately or simultaneously with multiple polynucleotide probes within one test sample. For example, several probes can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in miRNA levels over time. Increases or decreases in miRNA levels, as well as the absence of change in levels, can provide useful information about the disease status.

In some embodiments, a panel consisting of polynucleotide probes that selectively bind cancer-derived exosomal miRNAs correlated with one or more cancers can be constructed to provide relevant information related to the diagnosis or prognosis of cancer and management of subjects with cancer. Such a panel can be constructed, for example, using 1, 2, 3, 4, 5, 6, 7, 8, 9, 10, 15, 20, 30, 40, 50, 75, 100, 150, 200, 250, 300, 400, 500, or 1,000 individual polynucleotide probes. The analysis of a single probe or subsets of probes comprising a larger panel of probes could be carried out by one skilled in the art to optimize clinical sensitivity or specificity in various clinical settings. These include, but are not limited to ambulatory, urgent care, critical care, intensive care, monitoring unit, in-subject, out-subject, physician office, medical clinic, and health screening settings. Furthermore, one skilled in the art can use a single probe or a subset of additional probes comprising a larger panel of probes in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts.

In some embodiments, determining the amount of the one or more miRNAs comprises labeling the one or more miRNAs. The labeled miRNAs can then be captured with one or more polynucleotide probes that each selectively bind the one or more miRNAs.

As used herein, the terms "label" and "labeled" refer to the attachment of a moiety, capable of detection by spectroscopic, radiologic, or other methods, to a probe molecule. Thus, the terms "label" or "labeled" refer to incorporation or attachment, optionally covalently or non-covalently, of a detectable marker into/onto a molecule, such as a polynucleotide. Various methods of labeling polypeptides are known in the art and can be used. Examples of labels for polynucleotides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for antibodies, metal binding domains, epitope tags, etc.). In some embodiments, labels are attached by spacer arms of various lengths to reduce potential steric hindrance.

The analysis of miRNA levels utilizing polynucleotide probes can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion.

In some embodiments, the plurality of polynucleotide probes are each bound to a substrate. In some embodiments, the substrate comprises a plurality of addresses. Each address can be associated with at least one of the polynucleotide probes of the array. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" miRNA can be referenced as a moiety in a mobile phase (typically fluid), to be detected by probes ("target probes") which are bound to the substrate at the various regions.

Biopolymer arrays (e.g., polynucleotide microarrays) can be fabricated by depositing previously obtained biopolymers (such as from synthesis or natural sources) onto a substrate, or by in situ synthesis methods. Methods of depositing obtained biopolymers include, but are not limited to, loading then touching a pin or capillary to a surface, such as described in U.S. Pat. No. 5,807,522 or deposition by firing from a pulse jet such as an inkjet head, such as described in PCT publications WO 95/25116 and WO 98/41531, and elsewhere. The in situ fabrication methods include those described in U.S. Pat. No. 5,449,754 for synthesizing peptide arrays, and in U.S. Pat. No. 6,180,351 and WO 98/41531 and the references cited therein for polynucleotides, and may also use pulse jets for depositing reagents. Further details of fabricating biopolymer arrays by depositing either previously obtained biopolymers or by the in situ method are disclosed in U.S. Pat. Nos. 6,242,266, 6,232,072, 6,180,351, and 6,171,797. In fabricating arrays by depositing previously obtained biopolymers or by in situ methods, typically each region on the substrate surface on which an array will be or has been formed ("array regions") is completely exposed to one or more reagents. For example, in either method the array regions will often be exposed to one or more reagents to form a suitable layer on the surface that binds to both the substrate and biopolymer or biomonomer. In in situ fabrication the array regions will also typically be exposed to the oxidizing, deblocking, and optional capping reagents. Similarly, particularly in fabrication by depositing previously obtained biopolymers, it can be desirable to expose the array regions to a suitable blocking reagent to block locations on the surface at which there are no features from non-specifically binding to target.

Figure 2:
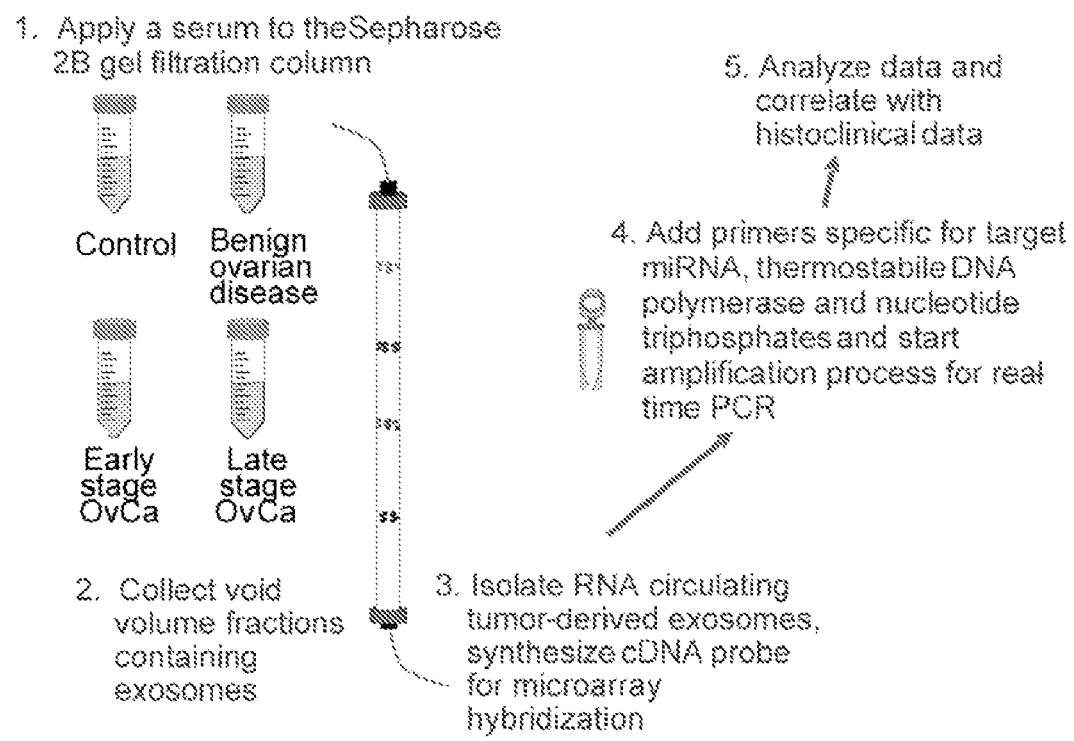
FIG. 2 is a schematic diagram showing exemplary methodology for isolating cancer-derived exosomes and miRNA from the exosomes, determining amounts of the miRNA by real-time PCR, and analyzing the data to determine if cancer is present and the stage of cancer in the subject tested.

Determining the amount of cancer-derived exosomal miRNAs can alternatively, or in addition to microarray analysis, comprise using real-time polymerase chain reaction (PCR), for example such as is disclosed in detail in the present Examples. Real-time PCR (RT-PCR) can provide accurate and rapid data as to presence and amount of miRNAs present in a sample. FIG. 2 provides a flowchart of an exemplary protocol for isolating and measuring exosomal-derived miRNAs by RT-PCR. Additional details of exemplary methodologies are set forth in the present Examples.

In some embodiments of the presently disclosed subject matter, a method for diagnosing potential adverse pregnancy outcomes in a subject is provided. The methodology disclosed in detail hereinabove for isolating exosomes comprising miRNAs and determining the amount of miRNA can be applied similarly to quantitating particular miRNAs associated with adverse pregnancy outcomes, with some modifications as now described.

For predicting adverse pregnancy outcomes, circulating exosomes derived from the placenta can be isolated from a biological sample, such as for example blood, or components thereof. The placenta, while derived from the fetus, is the only fetal tissue actually in contact with the maternal system. As such, exosomes produced by placental cells can circulate within the bloodstream of the mother. For isolation of placenta-derived exosomes, either anti-EpCAM antibodies (as used for tumor exosome isolation) or anti-placental type alkaline phosphatase antibodies (PLAP) affixed to magnetic beads can be utilized (see, e.g., FIG. 8).

For example, in some embodiments, the method comprises providing a biological sample from a subject and isolating exosomes comprising micro-RNAs (miRNAs) from the biological sample. An amount of one or more of the miRNAs is then determined and compared to one or more miRNA control levels. The subject can then be diagnosed with being at risk for an adverse pregnancy outcome if there is a measurable difference in the amount of the one or more miRNAs from the exosomes as compared to the one or more miRNA control levels. In some embodiments, the adverse pregnancy outcome is a disorder selected from the group consisting of preeclampsia, preterm birth (e.g., delivery before 32 weeks gestation), premature rupture of membranes, intrauterine growth restriction, and recurrent pregnancy loss.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

The presently disclosed subject matter discloses that miRNA can be found and isolated from exosomes in biological fluids. The isolated miRNA can be utilized as a diagnostic tool for cancer and adverse pregnancy outcomes. The present Examples provide support for these applications.

Materials and Methods for Examples 1-5

Patient Samples and Cell Lines

These Examples utilized as exemplary biological fluids sera derived from women diagnosed with serous papillary adenocarcinoma of the ovary (n=50; n=10 for stage I, n=10 for stage II, n=20 for stage III and n=10 for stage IV), age-matched women with benign ovarian adenoma (n=10), and age-matched women with no evidence of ovarian disease (n=10). Controls, patients with benign ovarian disease and stages III and IV ovarian cancer were selected based on age-matching to patients with early stage ovarian cancer. These Examples further includes data from investigations of primary tumor cell cultures, established from 6 women with Stage IIIc cyst adenocarcinoma of the ovary, and their corresponding pre-surgery sera samples. All of these materials were obtained under an informed consent approved by the University Human Studies Committee of the University of Louisville.

The primary ovarian tumor cell cultures were established in our laboratory and designated UL-1, UL-2, UL-3, UL-6, UL-B, and UL-O. UL-2 and UL-3 were derived from hereditary ovarian cancers, while UL-1, UL-6, UL-B, and UL-O were derived from spontaneous cancers. These ovarian tumor cells were grown in RPMI 1640 medium supplemented with 10% exosome-free (by ultrafiltration) fetal bovine serum, 0.1 mM nonessential amino acids, 1 mM sodium pyruvate, 200 mM L-glutamine, 100 mg/mL streptomycin and 100 IU/mL penicillin in a humidified 5% $CO_2$ atmosphere. Cell viability was evaluated by trypan blue exclusion and all cultures utilized were >95% viable.

Isolation of Circulating Exosomes

Tumor-derived exosomes were specifically isolated by a modified magnetic activated cell sorting (MACS) procedure, using anti-epithelial cell adhesion molecule (EpCAM). Our previous studies have demonstrated that exosomes from epithelial tumors express EpCAM on their surface and can be used for their selective isolation. Serum samples (2.5 ml) from normal controls, patients with benign disease, and patients with early stage ovarian cancer were incubated with anti-EpCAM coupled to magnetic microbeads (50 µl). These were mixed and incubated for 2 hrs at 4° C. A LD microcolumn was placed in the magnetic field of a MACS Separator and the column was rinsed with 500 µl Tris-buffered saline (TBS). The magnetic immune complexes were applied onto the column and unbound (unlabeled) material passed through and was discarded. The column was washed four times with 500 µl of TBS. The specifically selected exosomes were recovered by removing the column from the separator and placing it on a collection tube. TBS (1 ml) was be added to the column and the magnetically labelled exosomes were obtained by applying the plunger supplied with the column. The isolated exosomes/microbeads were diluted in IgG elution buffer (Pierce Chemical Co, Rockford, Ill.) and the complex was centrifuged at 10,000 rpm to separate the microbeads from the exosomes (supernatant). The supernatant was then centrifuged at 100,000 g for 1 hour at 4° C. The pelleted exosomes were resuspended in 250 µl phosphate-buffered saline (PBS) and these tumor derived exosomes were assayed for total protein. The quantity of protein was determined by the Bradford microassay method (Bio-Rad Laboratories, Hercules, Calif.), using bovine serum albumin (BSA) as a standard.

Transmission Electron Microscopy

For transmission electron microscopy, the pelleted exosomes were fixed in 2.5% (w/v) glutaraldehyde in PBS, dehydrated and embedded in Epon. Ultrathin sections (65 nm) were cut and stained with uranyl acetate and Reynold's lead citrate. The sections were examined in a Jeol 1210 transmission electron microscope.

Isolation and Profiling of miRNA

Total RNA was isolated from the tumor cells and exosomes using the mirVana miRNA isolation kit according to manufacturer's instructions (Ambion, Austin, Tex.). The RNA quality, yield, and size of miRNA fractions were analyzed using Agilent 2100 Bioanalyzer (Agilent Technologies, Foster City, Calif.). The isolated miRNAs were 3'-end labeled with Cy3 using the mirVana miRNA Array Labeling Kit (Ambion) and the Post Labeling Reactive Dye kit (Amersham Bioscience, Pittsburgh, Pa.). MicroRNA profiling was performed in duplicate by Ocean Ridge Biosciences (Jupiter, Fla.) using microarrays containing probes for 467 human mature miRNAs. This analysis used custom-developed miRNA arrays covering the 467 miRNAs present in the Sanger Institute mirBASE v9.0, consisting of 35-44-mer oligonucleotides, manufactured by Invitrogen and spotted in duplicate. After hybridization, the miRNA arrays were scanned using a GenePix 4000A array scanner (Axon Instruments, Union City, Calif.) and the raw data normalized and analyzed using GeneSpring 7.0 Software (Silicon Genetics, Redwood City, Calif.). Normalization was performed by expressing each miRNA replicate relative to control miRNA (Ambion) added to each sample, allowing comparisons between arrays. Threshold and $95^{th}$ percentile of negative controls (TPT95) were calculated based on hybridization signal from negative control probes including: 38 mismatch and shuffled control probes and 87 non-conserved *C. elegans* probes. To define sensitivity, NCode synthetic miRNA was spiked at 1/500,000 mass ratio into labeling reactions and the signal intensity was detected. For specificity, perfect match probes for miR-93, miR-27a, and miR-152 and 2 mismatches for each were used. The 2 base pair mismatch probes demonstrated a signal below or at TPT95 on all arrays.

To assess the stability of the exosomal profiling with storage and manipulations, sera from patients with ovarian cancer patients were obtained and aliquoted into four 4 ml samples. Tumor exosomes were isolated from the first aliquot by the MACS procedure immediately and total RNA isolated and stored at −70° C. until isolation of all samples. The remaining sera samples were stored at 4° C. for subsequent exosome isolation. Tumor exosomes were isolated from the second aliquot after 24 hours, from the third aliquot after 48 hours and from the fourth sample after 96 hours at 4° C. RNA was isolated from each exosome preparation and stored. In a similar study, 3 additional serum aliquots were stored at −70° C. for 7 to 28 days, prior to exosome and RNA isolations to mimic the use of banked specimens.

General Statistical Considerations

Data were analyzed using the statistical software package, SAS9.1 (SAS Institute, Cary, N.C.). The levels of circulating exosomes for each group of patients were defined as means±standard deviations from at least two separate experiments performed in triplicate. Comparisons between these groups were performed by one-way ANOVA, followed by the Tukey's multiple comparisons post-test comparing each population. Relative quantification of miRNA expression was calculated with the 2-ΔΔCt method (Applied Biosystems User Bulletin No. 2) and data were analyzed as log 10 of relative quantity (RQ) of the target miRNA, normalized with respect to control miRNA added to each sample, allowing comparisons between arrays. The miRNA distributions and correlations along with confidence intervals were calculated for each subset. Statistical significance was set as $p \leq 0.05$.

Example 1

Figure 3:
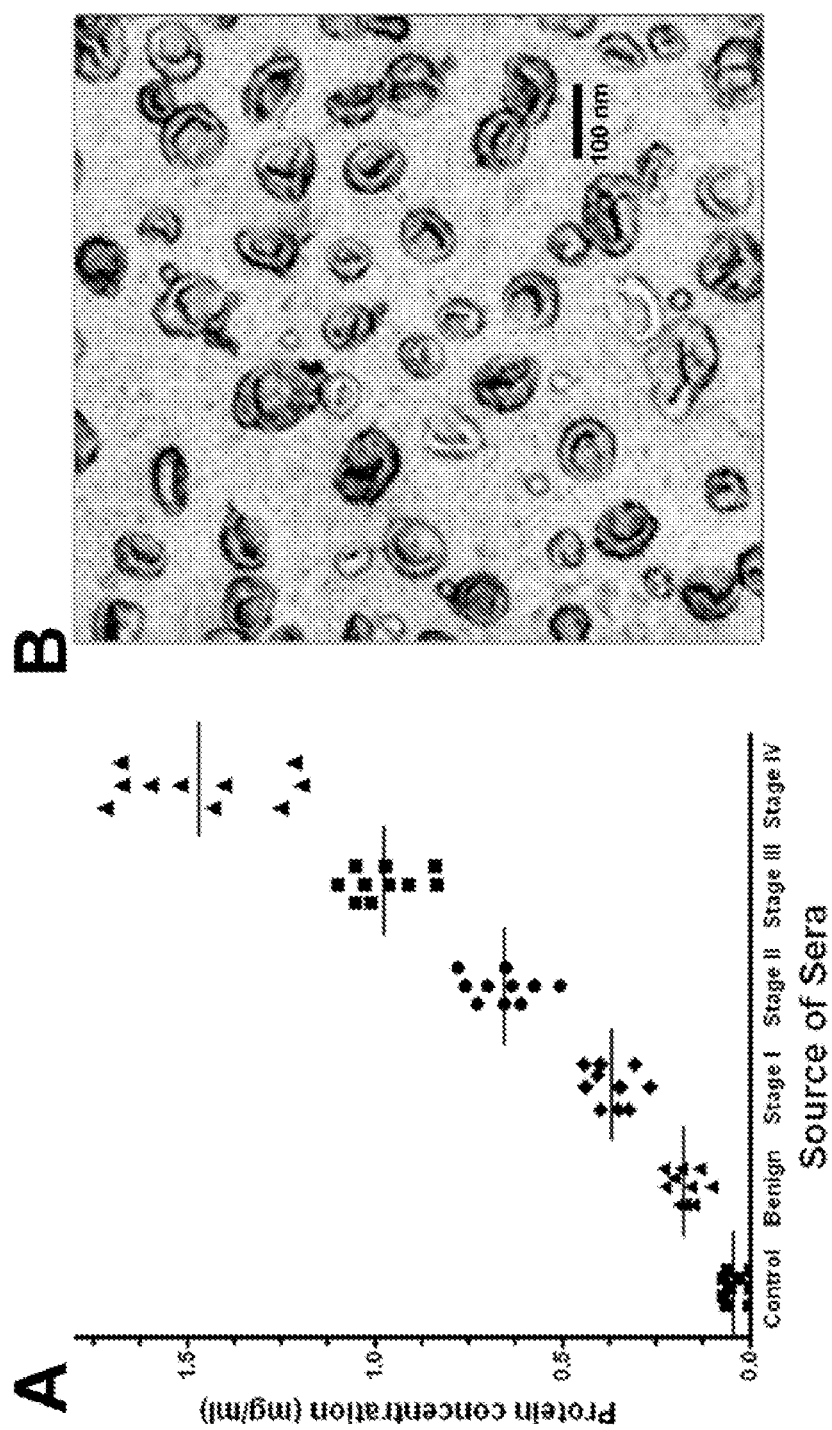
FIG. 3A is a graph showing the levels of circulating tumor-derived exosomes compared to stage of ovarian cancer. Exosomes were isolated from sera obtained from age-matched female controls (n=10), age-matched women with benign ovarian disease (n=10), and women diagnosed with ovarian cancer (n=10 for each stage). Levels of exosomes are presented as protein concentrations.
FIG. 3B is an electron micrograph of circulating exosomes isolated by magnetic beads. Ultrathin sections (65 nm) were cut and stained with uranyl acetate and Reynold's lead citrate. The sections were examined in a Jeol 1210 transmission electron microscope.

Presence of Circulating EpCAM-Positive Exosomes in Women with Benign and Malignant Ovarian Disease EpCAM-positive exosomes were specifically isolated using anti-EpCAM magnetic beads and these circulating exosomes were assayed for total protein and plotted versus stage of disease (FIG. 3A). The levels of EpCAM-positive exosomes in age-matched normal volunteers (control) were 0.039±0.030 mg/ml of exosomal protein, which represented the background of the assay. Patients diagnosed with benign ovarian disease possessed 0.149±0.065 mg/ml of exosomal protein, which was significantly elevated over controls. Patients diagnosed with ovarian cancer all exhibited significantly elevated levels of EpCAM-positive exosomes (compared to benign disease or controls). Women with Stage I ovarian cancer exhibited 0.320±0.056 mg/ml of circulating exosomal protein, which was significantly greater than both controls and benign disease ($p<0.01$). The levels of circulating exosomes increased as the stage progressed, with Stage II cancer having 0.640±0.053 mg/ml, Stage III possessing 0.995±0.084 mg/ml and Stage IV presenting with 1.42±0.228 mg/ml. Levels of exosomes associated with these three stages were significantly greater than women with benign disease or controls ($p<0.001$). The resulting fractions were further analyzed by electron microscopy, which demonstrated vesicular structures characteristic of exosomes (FIG. 3B). The exosomal nature of this material was further confirmed by the presence of tetraspanins, class I antigens, placental-type alkaline phosphatase by Western immunoblotting.

Example 2

Association of Small RNA with Tumor-Derived Exosomes

Figure 4:
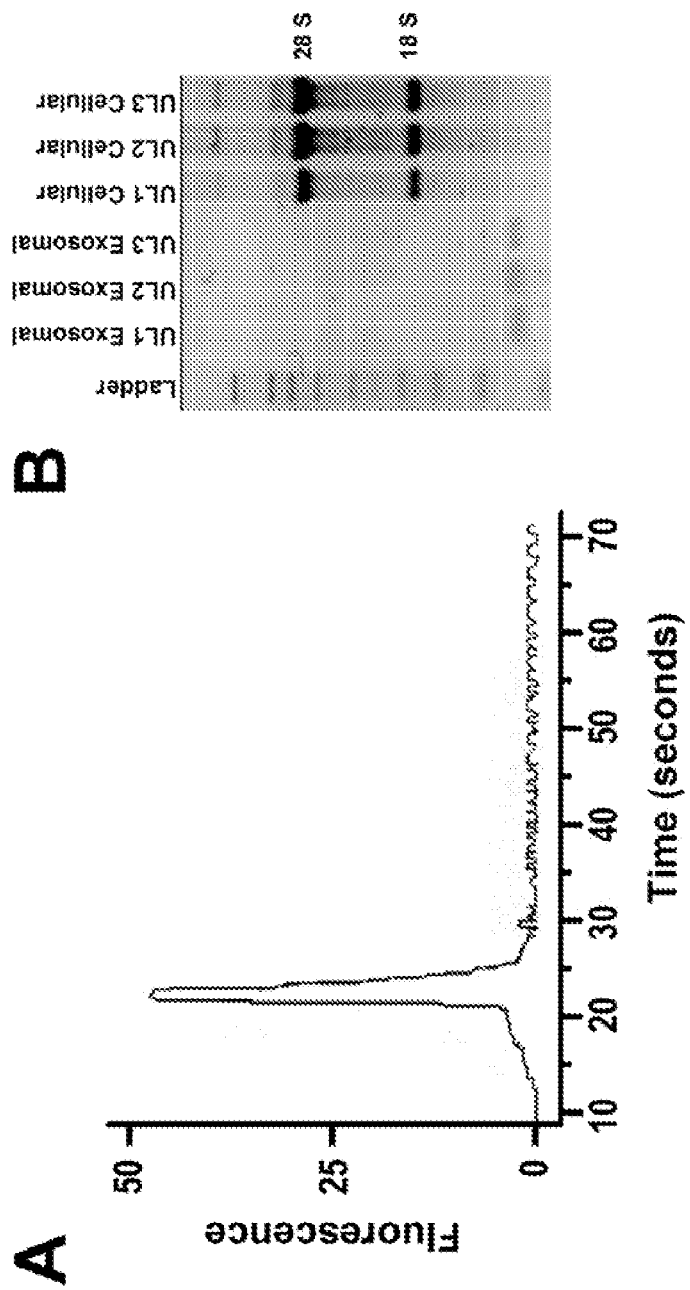
FIG. 4A is a graph showing the presence of small RNA associated with circulating EpCAM-positive exosomes from ovarian cancer patients. A representative analysis of the RNA isolated from tumor exosomes using Agilent 2100 Bioanalyzer is shown.
FIG. 4B is a photograph of an agarose gel (1%) separation of total RNA from circulating exosomes and corresponding tumors. This total RNA was used as the starting material for miRNA profiling.

To identify whether these isolated exosomes contained small RNAs, they were examined using a Bio-Analyzer 2100 (FIG. 4). This analysis identified the presence of a significant population of small RNA in the absence of 18S and 28S RNA, generally observed with cell-derived RNA. This material was subsequently used for miRNA profiling.

Example 3

Profiling of Exosome-Derived Versus Cell-Derived miRNA

The presence and levels of specific miRNAs from both cell-derived and exosome-derived miRNA were determined using microarray analysis (FIG. 1) probing for 467 miRNAs. Exemplary results are shown in Table 1. The miRNA profiles of our ovarian tumors confirmed the alterations, previously reported (Iorio et al., 2007). Further, we demonstrated that of the 467 miRNAs, 218 were above the normalized threshold, calculated based on the 95$^{th}$ percentile of the negative control probe signal in both the cells and exosomes (Table 2). Of the 218 positive miRNAs, the levels of 175 were not significantly different between the ovarian tumor cells and their corresponding exosomes. By comparison, 12 were present at a higher proportion in the cells, while 31 were present at elevated levels within exosomes.

Figure 5:
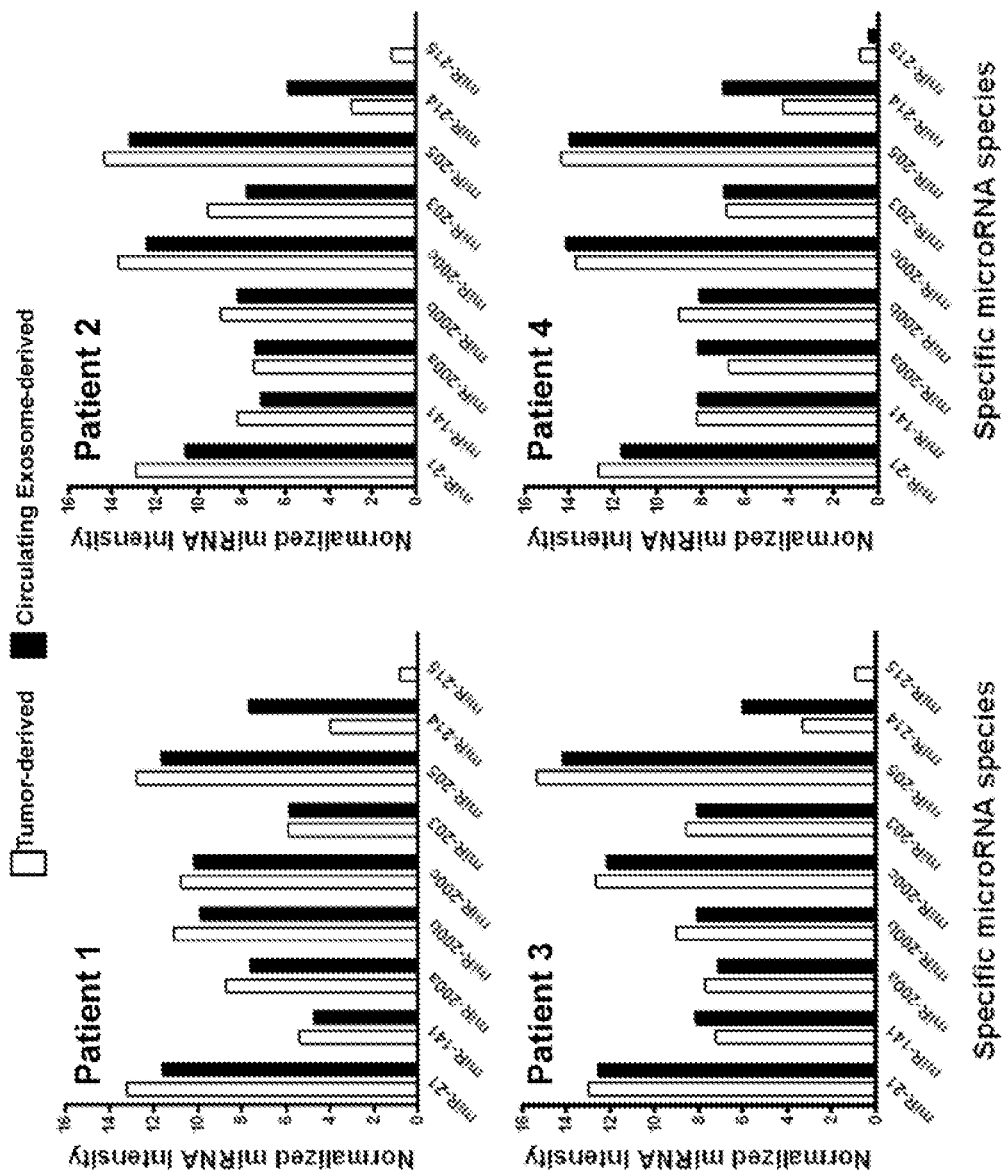
FIG. 5 is a series of graphs showing intensities for specific miRNAs derived from the advanced staged ovarian tumors (□) and from EpCAM-positive exosomes (■) isolated from the sera of these same patients. miR-21, miR-141, miR-200a, miR-200b, miR-200c, miR-203, miR-205, miR-214 have been demonstrated to be upregulated markers for ovarian cancer. Each bar presents the average intensities of duplicate samples with the results of four representative patients presented.

Previously, specific miRNAs were demonstrated to be overexpressed in human ovarian cancer cells (miR-21, miR-141, miR-200a, miR-200c, miR-200b, miR-203, miR-205, and miR-214). To correlate these findings with exosomal-derived material, RNA fractions were isolated from the original tumor cells and circulating tumor exosomes of the same patients (FIG. 5). Using microarray analysis, comparisons between tumor-derived miRNA profiles and peripheral blood-derived exosomal miRNAs indicated that they were not significantly different. Further, the levels of tumor-derived miRNA profiles exhibited a strong correlation with the levels of peripheral blood-derived exosomal miRNAs (for miR-21, r=0.77; miR-141, r=0.88; miR-200a, r=0.76; miR-200b, r=0.85; miR-200c, r=0.83; miR-203, r=0.85; miR-205, r=0.91; and miR-214, r=0.71).

TABLE 1

QUANTITATIVE COMPARISON OF miRNA IN CIRCULATING EXOSOMES AND TUMOR CELLS FROM CANCER SUBJECTS*

| Name | ID | Pat1 Ex 866A | Pat1 Cells 866B | Pat2 Ex 866C | Pat2 Cells 866D |
|---|---|---|---|---|---|
| hsa-miR-296 | 1098 | 5.05 | 4.33 | 4.24 | 4.79 |
| hsa-miR-330 | 1002 | 2.98 | 3.09 | 4.1 | 1.08 |
| hsa-miR-20a | 1007 | 11.46 | 11.35 | 12 | 11.93 |
| hsa-miR-28 | 1024 | 9.4 | 10.05 | 9.19 | 9.23 |
| hsa-miR-302c | 1032 | −0.58 | 3.08 | 3.5 | 1.08 |
| hsa-miR-302a | 1036 | 2.17 | 3.66 | 3.47 | 4.33 |
| hsa-miR-214 | 1057 | 6.58 | 3.93 | 6.17 | 2.99 |
| hsa-miR-99b | 1063 | 9.59 | 10.08 | 9.86 | 9.16 |
| hsa-miR-99a | 1068 | 3.81 | 4.53 | 7.34 | 6.46 |
| hsa-miR-10a | 1072 | 10.1 | 10.76 | 9.63 | 9.55 |
| hsa-let-7d | 1085 | 12.53 | 13.32 | 12.65 | 12.5 |
| hsa-miR-138 | 1089 | 5.37 | 5.26 | 4.18 | 3.61 |
| hsa-miR-140 | 1106 | 3.23 | 4.3 | 2.01 | 0.58 |
| hsa-miR-23a | 1114 | 14.51 | 15.08 | 14.99 | 14.78 |
| hsa-miR-215 | 1122 | 0.71 | 1.79 | 0.51 | 1.38 |
| hsa-miR-183 | 1127 | 9.08 | 9.63 | 8.99 | 8.9 |
| hsa-miR-32 | 1135 | 2 | 2.49 | 2.42 | 0.58 |
| hsa-miR-25 | 1139 | 11.34 | 11.3 | 12.23 | 12.01 |
| hsa-miR-218 | 1143 | 2.71 | 3.37 | 4.61 | 5.33 |
| hsa-miR-107 | 1163 | 11.68 | 12.18 | 11.29 | 11.31 |
| hsa-miR-145 | 1168 | 1.74 | 2.38 | 3.47 | 1.38 |
| hsa-miR-181a | 1172 | 11.9 | 12.62 | 11.35 | 11.15 |
| hsa-miR-125a | 1193 | 12.34 | 13.07 | 11.67 | 11.84 |
| hsa-miR-222 | 1198 | 12.37 | 12.53 | 11.77 | 10.99 |
| hsa-miR-372 | 1105 | −0.58 | 3.08 | 2.51 | 1.08 |
| hsa-miR-142-3p | 1253 | 2.72 | 3.06 | 4.59 | 3.91 |
| hsa-miR-198 | 1258 | 4.2 | 3.92 | 3.32 | 3.67 |
| hsa-miR-196a | 1263 | 4.78 | 5.07 | 3.42 | 4.04 |
| hsa-miR-16 | 1272 | 12.28 | 12.05 | 12.98 | 12.6 |
| hsa-miR-200a | 1287 | 8.29 | 8.72 | 7.17 | 7.44 |
| hsa-miR-18a | 1292 | 6.41 | 6.66 | 7.98 | 8.5 |
| hsa-miR-101 | 1297 | 4.62 | 4.87 | 5.55 | 6.01 |
| hsa-miR-195 | 1311 | 6.09 | 6.58 | 6.03 | 6.43 |
| hsa-miR-136 | 1203 | 3.69 | 3.77 | 3.52 | 3.65 |
| hsa-miR-153 | 1225 | 1.71 | 2.08 | 0.51 | 0.58 |
| hsa-miR-31 | 1227 | 8.97 | 9.49 | 9.6 | 9.32 |
| hsa-miR-33 | 1274 | 2.01 | 3.66 | 3.58 | 3.75 |
| hsa-miR-147 | 1278 | 4.65 | 2.95 | 3.47 | 3.17 |
| hsa-miR-106b | 1282 | 9.47 | 9.19 | 10.59 | 10.38 |
| hsa-miR-212 | 1288 | 2.67 | 1.81 | 2.89 | 3.75 |
| hsa-miR-15a | 1312 | 9.92 | 10.12 | 10.79 | 11.06 |
| hsa-miR-135b | 1331 | 4.51 | 4.03 | 4.42 | 4.07 |
| hsa-miR-92 | 1335 | 12.29 | 12.63 | 12.62 | 12.26 |
| hsa-miR-342 | 1349 | 9.14 | 9.62 | 8.36 | 8.39 |
| hsa-miR-205 | 1368 | 6.15 | 5.74 | 15.25 | 14.33 |
| hsa-miR-150 | 1385 | 4.02 | 2.87 | 3.33 | 1.38 |
| hsa-miR-149 | 1392 | 6.23 | 5.65 | 5.92 | 4.79 |
| hsa-let-7b | 1431 | 12.73 | 12.43 | 13.73 | 14.06 |
| hsa-miR-370 | 1445 | 4.14 | 3.7 | 4.37 | 2.58 |

TABLE 1-continued

QUANTITATIVE COMPARISON OF miRNA IN CIRCULATING EXOSOMES AND TUMOR CELLS FROM CANCER SUBJECTS*

| Name | ID | Pat1 Ex 866A | Pat1 Cells 866B | Pat2 Ex 866C | Pat2 Cells 866D |
|---|---|---|---|---|---|
| hsa-miR-206 | 1449 | 5.22 | 4.34 | 5.58 | 4.91 |
| hsa-miR-128a | 1350 | 7.54 | 7.9 | 8.06 | 8.01 |
| hsa-miR-197 | 1487 | 11.05 | 9.76 | 10.03 | 9.28 |
| hsa-miR-182 | 1506 | 10.11 | 10.89 | 10.09 | 10.41 |
| hsa-miR-553 | 1750 | 2.77 | 2.95 | 4.05 | 3.17 |
| hsa-miR-519d | 1766 | 2.17 | 3.28 | 0.51 | 3.04 |
| hsa-miR-520g | 1770 | −0.58 | 1.9 | 3.51 | 2.49 |
| hsa-miR-520e | 1774 | −0.58 | 1.79 | 0.51 | 3.75 |
| hsa-miR-329 | 1778 | 2.67 | 2.08 | 3.32 | 2.91 |
| hsa-miR-634 | 1782 | 6.69 | 2.64 | 3.32 | 1.08 |
| hsa-miR-614 | 1786 | 1.21 | −0.01 | 1.31 | 2.91 |
| hsa-miR-223 | 1467 | 2.71 | 2.49 | 4.17 | 3.17 |
| hsa-miR-485-5p | 1863 | 4.27 | 2.49 | 2.6 | 0.58 |
| hsa-miR-369-5p | 1867 | 2 | 1.49 | 0.51 | 0.58 |
| hsa-miR-575 | 1871 | 2.75 | 2.69 | 4.36 | 3.75 |
| hsa-miR-663 | 1891 | 5.41 | 5 | 6.17 | 5.76 |
| hsa-miR-520f__hsa-miR-520c | 1802 | 1.61 | 1.79 | 2.97 | 3.15 |
| hsa-miR-382 | 1806 | 4.48 | 4.14 | 4.04 | 3.25 |
| hsa-miR-655 | 1920 | 1.21 | 2.3 | 2.1 | 3.17 |
| hsa-miR-545 | 1932 | 2.5 | 2.66 | 2.92 | 3.58 |
| hsa-miR-502 | 1940 | 3.46 | 4.16 | 4.99 | 3.75 |
| hsa-miR-200a* | 1952 | 5.35 | 5.86 | 3.42 | 2.25 |
| hsa-miR-640 | 1956 | 2.24 | −0.51 | 2.51 | 0.58 |
| hsa-miR-514 | 1972 | 2 | 2.95 | 1.01 | 1.38 |
| hsa-miR-548b | 1988 | 1.92 | −0.01 | 2.51 | 0.58 |
| hsa-miR-609 | 1899 | 2.55 | 2.58 | 3.6 | 3.54 |
| hsa-miR-377 | 1929 | 1.74 | −0.01 | 2.6 | 0.58 |
| hsa-miR-433 | 1937 | 2.71 | 2.19 | 3.74 | 1.08 |
| hsa-miR-500 | 1957 | 4.67 | 4.88 | 6.34 | 5.8 |
| hsa-miR-652 | 1961 | 6.26 | 6.6 | 5.52 | 5.05 |
| hsa-miR-518c | 1981 | 0.92 | 1.81 | 3.68 | 1.38 |
| hsa-miR-561 | 1985 | −0.58 | 2.49 | 0.51 | 1.38 |
| hsa-miR-551a | 2018 | 3.77 | 3.27 | 4.06 | 3.91 |
| hsa-miR-525 | 2034 | −0.58 | 2.06 | 3.1 | 0.58 |
| hsa-miR-570 | 2054 | −0.58 | −0.51 | 0.51 | 0.58 |
| hsa-miR-617 | 2062 | 2 | 2.49 | 0.51 | 2.91 |
| hsa-miR-556 | 2070 | −0.58 | 1.81 | 1.31 | 1.08 |
| hsa-miR-551b | 2074 | 1.37 | 1.79 | 3.97 | 3.38 |
| hsa-miR-424 | 1993 | 5.87 | 5.84 | 4.54 | 4.79 |
| hsa-miR-612 | 1997 | 2.87 | 0.29 | 2.83 | 0.58 |
| hsa-miR-130a | 2005 | 8.07 | 8.66 | 9.08 | 9.2 |
| hsa-miR-429 | 2134 | 5.68 | 5.39 | 3.89 | 4.83 |
| hsa-miR-365 | 2138 | 8.7 | 8.73 | 7.51 | 7.31 |
| hsa-miR-29a | 2154 | 13.45 | 13.83 | 12.21 | 12.27 |
| hsa-miR-503 | 2162 | 5.44 | 6.25 | 1.31 | 4.39 |
| hsa-miR-624 | 2166 | −0.58 | 1.99 | 0.51 | 3.39 |
| hsa-miR-550 | 2097 | 4.34 | 4.26 | 3.89 | 2.58 |
| hsa-miR-581 | 2227 | 2.32 | 1.65 | 2.31 | 0.58 |
| hsa-miR-422a | 2263 | 8.33 | 8.48 | 9.59 | 9.25 |
| hsa-miR-449 | 2267 | 2.91 | 2.48 | 1.31 | 0.58 |
| hsa-miR-585 | 2271 | 3.58 | 3.74 | 4.51 | 4.12 |
| hsa-miR-92b | 2182 | 7.86 | 8.04 | 7.75 | 7.13 |
| hsa-miR-629 | 2316 | 6.12 | 5.93 | 6.82 | 7.03 |
| hsa-miR-580 | 2320 | −0.58 | 1.49 | 0.51 | 2.58 |
| hsa-miR-448 | 2324 | 1.74 | −0.51 | 2.83 | 0.58 |
| hsa-miR-592 | 2332 | 0.21 | 2.95 | 2.83 | 0.58 |
| hsa-miR-671 | 2839 | 4.15 | 3.98 | 4.21 | 0.58 |
| hsa-miR-767-3p | 2863 | 1.42 | 2.3 | 2.51 | 0.58 |
| hsa-miR-608 | 2279 | 3.74 | 1.29 | 2.47 | 0.58 |
| hsa-miR-210 | 2291 | 9.13 | 8.6 | 8.39 | 7.96 |
| hsa-miR-26a | 2299 | 12.6 | 12.61 | 12.27 | 12.73 |
| hsa-miR-493-5p | 2329 | 2 | 2.65 | 2.17 | 1.08 |
| hsa-miR-202* | 2337 | 2.55 | 2.08 | 3.32 | 1.88 |
| hsa-miR-454-5p | 2840 | 11.51 | 11.6 | 12.87 | 13.07 |
| hsa-miR-770-5p | 2844 | 2.24 | −0.01 | 1.01 | 0.58 |
| hsa-miR-769-3p | 2865 | 3.8 | 3.74 | 3.01 | 2.88 |
| hsa-miR-758 | 2869 | −0.58 | −0.51 | 0.51 | 0.58 |
| hsa-miR-765 | 2864 | 5.35 | 5.13 | 6.08 | 5.77 |
| hsa-miR-301 | 1103 | 3.96 | 4.08 | 4.04 | 4.68 |
| hsa-miR-191 | 1017 | 9.84 | 10.87 | 11.01 | 10.9 |
| hsa-miR-93 | 1029 | 9.68 | 9.58 | 10.93 | 9.75 |
| hsa-let-7f | 1033 | 11.59 | 12.43 | 11.79 | 11.94 |
| hsa-miR-373 | 1037 | 3.54 | 2.4 | 4.51 | 3.08 |
| hsa-miR-200b | 1042 | 10.9 | 11.07 | 10.17 | 9.02 |
| hsa-miR-100 | 1064 | 7.25 | 6.69 | 7.81 | 5.54 |
| hsa-miR-324-3p | 1082 | 5.67 | 4.71 | 5.64 | 3.99 |
| hsa-miR-34b | 1096 | 3.27 | 3.49 | 3.83 | 4.54 |
| hsa-miR-324-5p | 1115 | 3.84 | 2.29 | 4.16 | 4.49 |
| hsa-miR-199a* | 1124 | 1.82 | 2.24 | 1.01 | 4.17 |
| hsa-miR-103 | 1164 | 11.27 | 10.65 | 11.3 | 9.18 |
| hsa-miR-220 | 1173 | 3.67 | 3.04 | 4.26 | 3.99 |
| hsa-miR-151 | 1199 | 9.73 | 9.47 | 10.22 | 10.45 |
| hsa-miR-186 | 1141 | 4.72 | 4.93 | 3.86 | 4.49 |
| hsa-miR-128b | 1153 | 6.29 | 6.26 | 6.7 | 6.1 |
| hsa-miR-130b | 1165 | 7.72 | 6.96 | 7.99 | 6.49 |
| hsa-miR-338 | 1174 | 2.42 | 2.66 | 2.67 | 2.91 |
| hsa-miR-199b | 1178 | 1.98 | −0.01 | 3.67 | 3.46 |
| hsa-miR-125b | 1182 | 9.34 | 8.81 | 9.86 | 8.11 |
| hsa-miR-122a | 1243 | 5.11 | 3.49 | 4.97 | 4.71 |
| hsa-miR-30d | 1251 | 11.72 | 11.93 | 11.32 | 11.69 |
| hsa-miR-203 | 1260 | 1.42 | 2.9 | 9.1 | 9.56 |
| hsa-let-7c | 1268 | 11.91 | 12.72 | 13.09 | 12.47 |
| hsa-miR-216 | 1294 | 2 | 2.45 | 2.71 | 3.38 |
| hsa-miR-15b | 1313 | 11.75 | 12.27 | 12.66 | 12.77 |
| hsa-miR-192 | 1205 | 7.05 | 8.48 | 6 | 6.14 |
| hsa-miR-133a | 1215 | 3.27 | 3.07 | 3.82 | 4.11 |
| hsa-miR-126 | 1380 | 6.42 | 6.42 | 5.94 | 7.51 |
| hsa-miR-326 | 1393 | 3.32 | 0.29 | 0.51 | 3.17 |
| hsa-miR-98 | 1423 | 6.58 | 7.21 | 6.9 | 7.33 |
| hsa-let-7g | 1432 | 10.8 | 11.21 | 10.01 | 10.06 |
| hsa-miR-190 | 1437 | 3.16 | 3.57 | 4.02 | 4.29 |
| hsa-miR-189 | 1442 | 2.59 | 2.79 | 2.92 | 3.38 |
| hsa-miR-137 | 1339 | 2.66 | 3.06 | 4.36 | 3.88 |
| hsa-miR-105 | 1345 | 2.37 | 2.48 | 4.32 | 3.17 |
| hsa-miR-96 | 1507 | 4.66 | 4.17 | 4.58 | 4.58 |
| hsa-miR-519e | 1767 | −0.08 | 2.3 | 2.83 | 1.08 |
| hsa-miR-520a | 1771 | 1.42 | 1.99 | 3.1 | 0.58 |
| hsa-miR-451 | 1783 | 1 | −0.51 | 3.32 | 2.58 |
| hsa-miR-523 | 1787 | −0.58 | −0.51 | 0.51 | 0.58 |
| hsa-miR-299-5p | 1458 | 1.74 | 2.06 | 2.51 | 0.58 |
| hsa-miR-95 | 1482 | 3.94 | 3.78 | 2.71 | 3.08 |
| hsa-miR-593 | 1832 | 4.92 | 1.08 | 4.1 | 2.91 |
| hsa-miR-574 | 1840 | 11.34 | 9.36 | 11.12 | 9.45 |
| hsa-miR-202 | 1864 | 2.59 | 1.9 | 2.97 | 3.67 |
| hsa-miR-519b | 1799 | −0.08 | 3.49 | 3.97 | 3.83 |
| hsa-miR-520d | 1803 | 2.58 | 3.56 | 3.89 | 4.36 |
| hsa-miR-622 | 1829 | 1.42 | 2.66 | 0.51 | 1.38 |
| hsa-miR-483 | 1845 | 8.06 | 3.91 | 7.36 | 4.34 |
| hsa-miR-383 | 1865 | 2.17 | 1.95 | 0.51 | 1.88 |
| hsa-miR-29b | 1869 | 6.67 | 6.05 | 5.9 | 6.65 |
| hsa-miR-613 | 1881 | 2.42 | −0.01 | 1.31 | 0.58 |
| hsa-miR-453 | 1904 | 3.93 | 3.59 | 4.76 | 4.17 |
| hsa-miR-23b | 1930 | 13.2 | 13.81 | 12.99 | 13.61 |
| hsa-miR-501 | 1942 | 2.87 | 2.72 | 1.31 | 3.25 |
| hsa-miR-517c | 1946 | 3.01 | 3.02 | 4.36 | 4.39 |
| hsa-miR-625 | 1897 | 6.54 | 7.16 | 5.67 | 5.65 |
| hsa-miR-630 | 1905 | 2.74 | 1.49 | 2.92 | 3.49 |
| hsa-miR-644 | 1913 | 0.21 | 2.29 | 2.51 | 2.91 |
| hsa-miR-527 | 2039 | 3.42 | 1.87 | 2.51 | 1.08 |
| hsa-miR-589 | 2055 | −0.08 | −0.51 | 1.31 | 0.58 |
| hsa-miR-508 | 2071 | 2.81 | 2.79 | 3.21 | 4.04 |
| hsa-miR-449b | 2083 | 2.41 | 2.48 | 3.97 | 2.58 |
| hsa-miR-603 | 1990 | 4.74 | 2.84 | 3.76 | 0.58 |
| hsa-miR-200c | 2131 | 4.25 | 3.75 | 13.3 | 13.7 |
| hsa-miR-29c | 2155 | 2.75 | 3.24 | 3.6 | 4.2 |
| hsa-miR-411 | 2167 | −0.58 | −0.51 | 0.51 | 0.58 |
| hsa-miR-455 | 2179 | 2.87 | 2.52 | 2.6 | 0.58 |
| hsa-miR-378 | 2208 | 2.24 | 2.3 | 3.6 | 2.91 |
| hsa-miR-638 | 2212 | 7.37 | 6.34 | 8.56 | 7.57 |
| hsa-miR-518f* | 2220 | −0.58 | −0.51 | 3.17 | 3.67 |
| hsa-let-7i | 2244 | 12.8 | 13.03 | 10.86 | 10.79 |
| hsa-miR-422b | 2264 | 9.17 | 8.72 | 10.51 | 10.23 |
| hsa-miR-193b | 2268 | 9.68 | 8.44 | 8.63 | 7.54 |

TABLE 1-continued

QUANTITATIVE COMPARISON OF miRNA IN CIRCULATING EXOSOMES AND TUMOR CELLS FROM CANCER SUBJECTS*

| Name | ID | Pat1 Ex 866A | Pat1 Cells 866B | Pat2 Ex 866C | Pat2 Cells 866D |
|---|---|---|---|---|---|
| hsa-miR-491 | 2272 | 1.74 | 0.79 | 2.81 | 0.58 |
| hsa-miR-484 | 2191 | 8.32 | 7.81 | 8.29 | 7.72 |
| hsa-miR-623 | 2203 | 1.74 | 2.45 | 0.51 | 0.58 |
| hsa-miR-486 | 2209 | 3.86 | 3.3 | 4.2 | 4.6 |
| hsa-miR-639 | 2213 | 1.87 | 1.49 | 2.31 | 1.38 |
| hsa-miR-517a__hsa-miR-517b | 2217 | 2.11 | 2.56 | 3.87 | 3.28 |
| hsa-miR-645 | 2221 | 3.12 | 1.29 | 0.51 | 2.58 |
| hsa-miR-146b | 2237 | 5.56 | 5.29 | 4.21 | 5.59 |
| hsa-miR-571 | 2249 | 3.33 | 2.99 | 4.1 | 2.91 |
| hsa-miR-191* | 2257 | 2.42 | 2.95 | 1.31 | 0.58 |
| hsa-miR-7 | 2261 | 2.44 | 3.02 | 2.51 | 3.54 |
| hsa-miR-647 | 2269 | 4.95 | 4.27 | 5.5 | 6.01 |
| hsa-miR-637 | 2273 | 4.65 | 2.84 | 4.9 | 4.17 |
| hsa-miR-30b | 2280 | 9.94 | 9.87 | 9.86 | 9.66 |
| hsa-miR-431 | 2288 | 1.74 | −0.01 | 0.51 | 2.58 |
| hsa-miR-452 | 2292 | 4.68 | 5.15 | 5.14 | 5.85 |
| hsa-miR-361 | 2296 | 10.36 | 11.32 | 10.53 | 10.83 |
| hsa-miR-576 | 2314 | 1.87 | −0.51 | 2.83 | 0.58 |
| hsa-miR-432 | 2326 | 3.74 | 3.47 | 3.51 | 2.58 |
| hsa-miR-375 | 2342 | 3.42 | 2.15 | 0.51 | 3.75 |
| hsa-miR-766 | 2841 | 9.66 | 6.37 | 8.18 | 7.59 |
| hsa-miR-768-3p | 2845 | 9.89 | 9.61 | 9.2 | 9.48 |
| hsa-miR-769-5p | 2861 | 4.03 | 4.07 | 4.47 | 3.46 |
| hsa-miR-513 | 2301 | 3.8 | 2.56 | 3.97 | 4.38 |
| hsa-miR-362 | 2017 | 2.93 | 4.53 | 4.88 | 4.38 |
| hsa-miR-565 | 2045 | 7.04 | 4.89 | 5.13 | 6.45 |
| hsa-miR-30e-3p | 2053 | 8.97 | 9.4 | 7.84 | 7.61 |
| hsa-miR-320 | 1005 | 12.75 | 13.28 | 13.11 | 13.09 |
| hsa-miR-132 | 1014 | 4.94 | 6.57 | 6.22 | 7.04 |
| hsa-miR-193a | 1018 | 4.56 | 4.32 | 3.66 | 4.58 |
| hsa-miR-22 | 1022 | 8.71 | 8.95 | 8.69 | 8.79 |
| hsa-miR-224 | 1026 | 6.69 | 7.1 | 6.4 | 6.96 |
| hsa-let-7a | 1030 | 13.37 | 14.07 | 14.63 | 14.91 |
| hsa-miR-302d | 1034 | 2.32 | 2.74 | 3.76 | 3.28 |
| hsa-miR-369-3p | 1038 | 2.72 | 2.38 | 4.68 | 3.83 |
| hsa-miR-106a | 1006 | 12.01 | 12.48 | 12.09 | 12.36 |
| hsa-miR-181c | 1015 | 5.67 | 6.09 | 4.64 | 4.27 |
| hsa-miR-17-5p | 1031 | 11.57 | 11.85 | 11.34 | 11.83 |
| hsa-miR-302b | 1035 | −0.08 | 2.66 | 3.26 | 4.04 |
| hsa-miR-19b | 1039 | 10.14 | 10.07 | 11.3 | 11.47 |
| hsa-miR-24 | 1044 | 12.91 | 13.2 | 13.13 | 13.4 |
| hsa-miR-17-3p | 1079 | 4.95 | 5.02 | 4.83 | 5.34 |
| hsa-miR-221 | 1088 | 13.67 | 13.73 | 12.88 | 12.76 |
| hsa-miR-335 | 1146 | −0.58 | −0.51 | 6.66 | 7.68 |
| hsa-miR-199a | 1167 | 2.31 | −0.51 | 0.51 | 3.17 |
| hsa-miR-126* | 1171 | 3.12 | 1.95 | 3.68 | 3.15 |
| hsa-miR-337 | 1175 | 2.22 | −0.51 | 3.97 | 2.91 |
| hsa-miR-181a* | 1179 | 5.67 | 5.34 | 5.91 | 5.76 |
| hsa-miR-331 | 1183 | 6.46 | 5.25 | 5.55 | 4.95 |
| hsa-miR-340 | 1187 | 2.96 | 2.99 | 3.86 | 4.17 |
| hsa-miR-188 | 1116 | 3.94 | 3.31 | 3.86 | 4.39 |
| hsa-miR-9 | 1231 | 2.96 | 3.25 | 4 | 4.53 |
| hsa-miR-34a | 1235 | 6.95 | 6.56 | 7.17 | 7.33 |
| hsa-miR-30c | 1252 | 13.78 | 13.97 | 12.46 | 12.24 |
| hsa-miR-19a | 1271 | 5.93 | 5.76 | 8.01 | 8.36 |
| hsa-miR-371 | 1276 | 3.67 | 2.19 | 3.36 | 3.38 |
| hsa-miR-10b | 1301 | 6.91 | 7.36 | 7.73 | 8.03 |
| hsa-miR-21 | 1315 | 13.13 | 13.2 | 12.28 | 12.88 |
| hsa-miR-217 | 1206 | 2.53 | 2.49 | 0.51 | 3.57 |
| hsa-miR-302b* | 1210 | 1.87 | 2.49 | 2.51 | 2.99 |
| hsa-miR-135a | 1216 | 2.41 | 3.62 | 3.47 | 3.89 |
| hsa-miR-148a | 1361 | 3 | 1.45 | 6.87 | 7.35 |
| hsa-miR-339 | 1366 | 4.85 | 4.26 | 5.12 | 5.2 |
| hsa-miR-187 | 1381 | 3.69 | 2.4 | 4.21 | 3.75 |
| hsa-miR-346 | 1390 | 5.77 | 3.2 | 4.09 | 4.87 |
| hsa-miR-146a | 1409 | 9.7 | 9.88 | 7.17 | 7.56 |
| hsa-miR-143 | 1415 | −0.58 | −0.51 | 2.51 | 3.75 |
| hsa-miR-219 | 1426 | 2 | 1.81 | 3.32 | 4.04 |
| hsa-miR-185 | 1451 | 8.4 | 8.73 | 9.33 | 9.46 |
| hsa-miR-328 | 1455 | 7.15 | 4.5 | 4.92 | 4.33 |
| hsa-miR-196b | 1321 | 4.65 | 4.44 | 5.08 | 5.68 |
| hsa-miR-204 | 1489 | 0.71 | 2.49 | 0.51 | 1.38 |
| hsa-miR-133b | 1498 | −0.58 | −0.51 | 0.51 | 0.58 |
| hsa-miR-129 | 1512 | 6.33 | 6.08 | 7.2 | 8.02 |
| hsa-miR-649 | 1756 | 3.32 | 2.93 | 3.17 | 2.17 |
| hsa-miR-522 | 1776 | 2.87 | 3.4 | 5.74 | 5.87 |
| hsa-miR-618 | 1788 | 2.22 | 1.65 | 0.51 | 1.08 |
| hsa-miR-30a-5p | 1460 | 12.45 | 12.55 | 11.09 | 11.04 |
| hsa-miR-27a | 1485 | 11.64 | 11.67 | 11.97 | 12.27 |
| hsa-miR-30a-3p | 1505 | 12.22 | 12.57 | 10 | 10.48 |
| hsa-miR-494 | 1753 | 4.47 | 3.87 | 6.12 | 5.48 |
| hsa-miR-20b | 1769 | 10.41 | 10.8 | 10.92 | 11.2 |
| hsa-miR-521 | 1785 | 3.42 | 0.49 | 3.31 | 3.75 |
| hsa-miR-363 | 1822 | −0.58 | −0.51 | 3.32 | 1.08 |
| hsa-miR-181b | 1830 | 11.53 | 11.96 | 10.84 | 11.02 |
| hsa-miR-18a* | 1850 | 4.52 | 2.99 | 4.97 | 3.83 |
| hsa-miR-423 | 1874 | 8.9 | 8.85 | 9.09 | 8.46 |
| hsa-miR-595 | 1805 | 9.11 | 6.55 | 8.47 | 6.49 |
| hsa-miR-487b | 1817 | 4.65 | 4.3 | 5.22 | 5.53 |
| hsa-miR-425-3p | 1943 | 4.14 | 4.02 | 3.39 | 3.96 |
| hsa-miR-594 | 1951 | 10.94 | 10.48 | 11.55 | 11.22 |
| hsa-miR-532 | 1959 | 5.87 | 5.79 | 6.62 | 6.14 |
| hsa-miR-544 | 1971 | 1.08 | 2.49 | 1.01 | 2.91 |
| hsa-miR-512-3p | 1910 | 2.56 | 2.74 | 4.41 | 3.83 |
| hsa-miR-526a | 2036 | −0.58 | −0.51 | 5.78 | 5.87 |
| hsa-miR-619 | 2044 | 2.01 | 1.49 | 1.01 | 4.08 |
| hsa-miR-578 | 2048 | 3.54 | 2.79 | 3.17 | 2.38 |
| hsa-miR-492 | 2060 | −0.08 | 1.49 | 2.71 | 2.67 |
| hsa-miR-590 | 2064 | 3.27 | 3.4 | 5.51 | 5.08 |
| hsa-miR-515-3p | 2068 | 1.74 | 2.88 | 3.51 | 1.08 |
| hsa-miR-539 | 2080 | 2.74 | 1.81 | 2.51 | 4.28 |
| hsa-miR-497 | 1995 | 3.05 | 3.11 | 3.26 | 0.58 |
| hsa-miR-152 | 2007 | 7.72 | 8.44 | 6.59 | 7.2 |
| hsa-miR-181d | 2011 | 8.56 | 8.9 | 7.83 | 7.49 |
| hsa-miR-660 | 2144 | 5.3 | 5.36 | 6.62 | 6.8 |
| hsa-miR-584 | 2176 | 10.1 | 10.43 | 7.6 | 7.99 |
| hsa-miR-511 | 2109 | 2.59 | −0.01 | 2.83 | 2.91 |
| hsa-miR-141 | 2117 | −0.58 | −0.51 | 7.91 | 8.21 |
| hsa-miR-18b | 2125 | 5.18 | 5.41 | 6.65 | 6.98 |
| hsa-miR-582 | 2141 | −0.58 | −0.51 | 4.9 | 4.87 |
| hsa-miR-586 | 2173 | 2.11 | 1.49 | 2.47 | 1.08 |
| hsa-miR-505 | 2184 | 5.06 | 5.45 | 4.16 | 4.58 |
| hsa-miR-642 | 2200 | 4.22 | 1.15 | 2.42 | 0.58 |
| hsa-miR-628 | 2222 | 3.59 | 2.19 | 2.17 | 3.83 |
| hsa-miR-425-5p | 2234 | 8.86 | 9.29 | 9.01 | 8.92 |
| hsa-miR-661 | 2274 | 2.42 | 1.81 | 0.51 | 0.58 |
| hsa-miR-421 | 2185 | 4.06 | 5.49 | 6.41 | 6.43 |
| hsa-miR-27b | 2303 | 10.82 | 11.2 | 11.39 | 11.55 |
| hsa-miR-651 | 2335 | 1.71 | 1.69 | 3.39 | 2.91 |
| hsa-miR-557 | 2339 | 3.37 | 2.49 | 3.51 | 0.58 |
| hsa-miR-801 | 2846 | 5.97 | 3.08 | 4.59 | 1.88 |
| hsa-miR-768-5p | 2854 | 8.68 | 8.01 | 8.5 | 8.38 |
| hsa-miR-454-3p | 2858 | 3 | 3.37 | 4.32 | 3.78 |
| hsa-miR-498 | 2298 | 2.87 | −0.51 | 0.51 | 2.67 |
| hsa-miR-148b | 1362 | 6.83 | 6.76 | 6.82 | 6.69 |
| hsa-miR-194 | 1416 | 8.57 | 8.28 | 4.64 | 5.81 |
| hsa-let-7e | 1421 | 7.42 | 9.18 | 8.74 | 9.52 |
| hsa-miR-345 | 1444 | 4.63 | 4.62 | 3.68 | 3.17 |
| hsa-miR-155 | 1476 | 8.21 | 9.31 | 4.32 | 6.17 |
| hsa-miR-374 | 1480 | 1.42 | 1.79 | 0.51 | 1.38 |
| hsa-miR-26b | 1484 | 9.52 | 10 | 9.72 | 10.43 |

*Raw data was background-subtracted, Log2-transformed, and normalized. Intensity for each oligo probe is based on averaging of duplicate spots. Normalized threshold is calculated based on log2(5 * stdev of non-spot background + trim mean negative control probe signal)

TABLE 2

ASSOCIATION OF miRNA WITH PERIPHERAL BLOOD-DERIVED TUMOR EXOSOMES COMPARED WITH miRNA ISOLATED FROM THEIR CORRESPONDING TUMORS
Association of microRNA with peripheral blood-derived tumor exosomes compared with microRNA isolated from their corresponding tumors.

| Elevated in cells | Equal between cells & exosomes | Elevated in exosomes |
|---|---|---|
| miR-218, miR-196a, miR-195, miR-15a, miR-519d, miR-382, miR-503, miR-34b, miR-520d, miR-29c, miR-135a, miR-155 | miR-296, miR-20a, miR-28, miR-302a, miR-99a, miR-99b, miR-10a, let-7a, let-7b, let-7c, let-7d, let-7f, let-7g, let-7i, miR-138, miR-23a, miR-183, miR-25, miR-107, miR-181a, miR-125a, miR-222, miR-198, miR-16, miR-200a, miR-18a, miR-101, miR-136, miR-31, miR-106b, miR-92, miR-342, miR-128a, miR-182, miR-663, miR-502, miR-500, miR-652, miR-424, miR-130a, miR-429, miR-365, miR-29a, miR-550, miR-422a, miR-585, miR-92b, miR-629, miR-671, miR-210, miR-26a, miR-454-5p, miR-769-3p, miR-765, miR-301, miR-191, miR-93, miR-200b, miR-100, miR-324-5p, miR-220, miR-151, miR-186, miR-128b, miR-130b, miR-125b, miR-122a, miR-30d, miR-203, miR-15b, miR-192, miR-133a, miR-126, miR-98, miR-190, miR-137, miR-105, miR-96, miR-95, miR-519b, miR-29b, miR-453, miR-23b, miR-517c, miR-625, miR-200c, miR-193a, miR-22, miR-224, miR-369-3p, miR-106a, miR-181c, miR-17-5p, miR-19b, miR-24, miR-17-3p, miR-221, miR-335, miR-126, miR-181a, miR-331, miR-188, miR-9, miR-34a, miR-30c, miR-19a, miR-371, miR-10b, miR-21, miR-148a, miR-339, miR-187, miR-346, miR-146a, miR-185, miR-328, miR-196b, miR-129, miR-522, miR-30a-5p, miR-27a, miR-30a-3p, miR-494, miR-20b, miR-521, miR-181b, miR-423, miR-487b, miR-425-3p, miR-594, miR-532, miR-512-3p, miR-526a, miR-578, miR-638, miR-422b, miR-484, miR-486, miR-645, miR-146b, miR-571, miR-647, miR-637, miR-30b, miR-452, miR-361, miR-432, miR-375, miR-766, miR-768-3p, miR-769-5p, miR-513, miR-362, miR-565, miR-30e-3p, miR-320, miR-590, miR-152, miR-181d, miR-660, miR-584, miR-141, miR-18b, miR-582, miR-505, miR-628, miR-425-5p, miR-421, miR-27b, miR-768-5p, miR-454-3p, miR-148b, miR-194, miR-345, miR-26b | miR-214, miR-140, miR-147, miR-135b, miR-205, miR-150, miR-149, miR-370, miR-206, miR-197, miR-634, miR-485-5p, miR-612, miR-608, miR-202, miR-373, miR-324-3p, miR-103, miR-593, miR-574, miR-483, miR-527, miR-603, miR-649, miR-18a, miR-595, miR-193b, miR-642, miR-557, miR-801, let-7e |

Example 4

Exosomal miRNA Correlation with Presence and Stage of Disease

Figure 6:
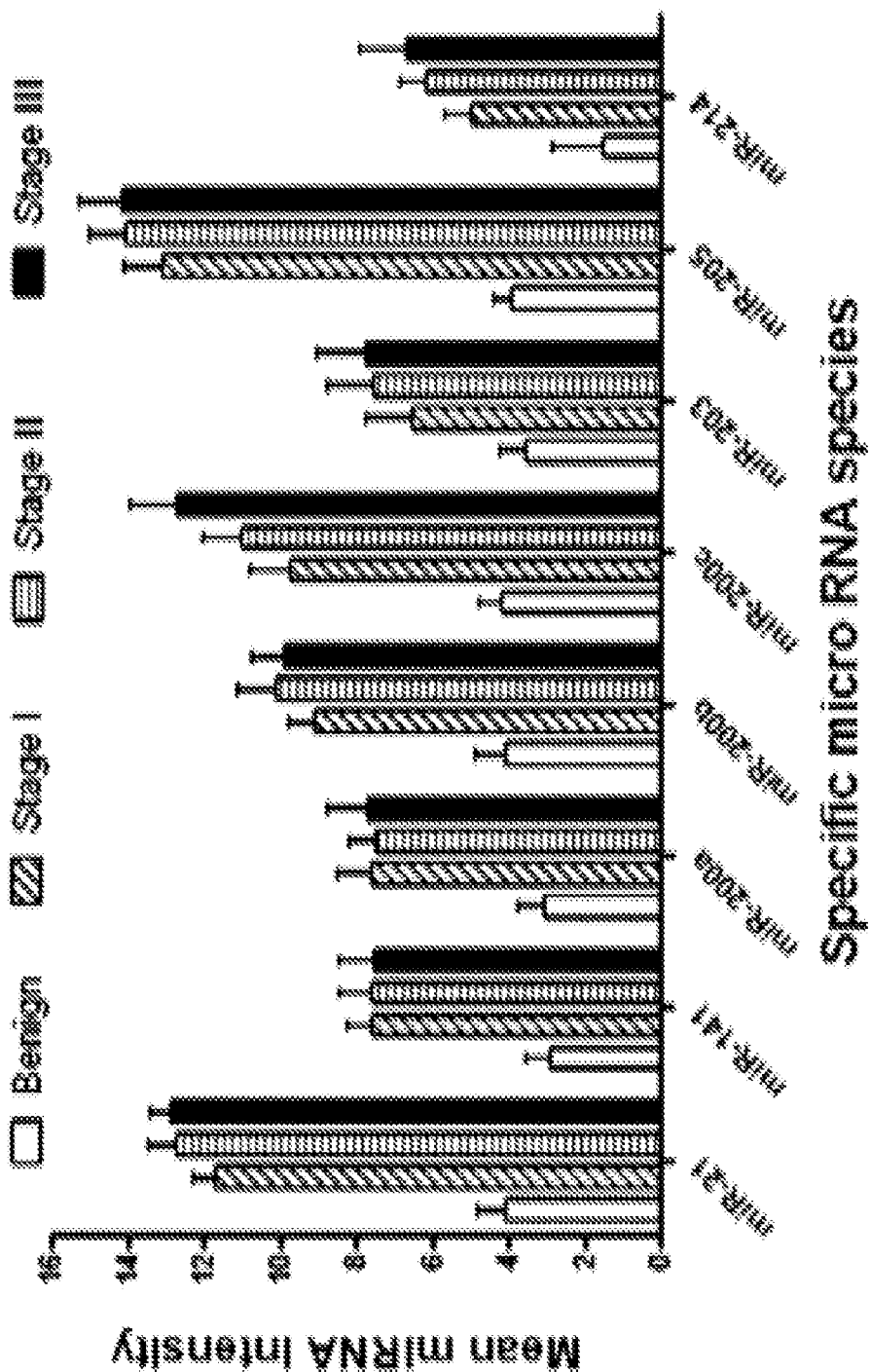
FIG. 6 is a graph showing intensities for specific miRNAs derived from EpCAM-positive exosomes isolated from the peripheral blood (2.5 mL) of the patients with benign ovarian disease and patients with ovarian cancer. Patients with ovarian cancer were separated between Stages I, II, and III. The bars represent the mean±standard deviation of the normalized intensities of each group of patients (n=10 for each group).

Our previous comparisons between tumor and circulating exosomes were performed with advanced stage patients. To compare the associations of specific miRNAs with the presence of disease across various stages, the mean intensities of exosomal miRNAs were determined. The presence of the 8 diagnostic miRNAs among patients with stage I, II and III were not significantly different for most of these miRNAs (FIG. 6). miR-200c and miR-214 were lower in patients with stage I, compared to stages II and III. However, in all cases, these miRNAs were significantly elevated over the levels detected in exosomes derived from benign disease. The small RNA fraction could not be demonstrated in normal controls and attempts to assess the presence of miRNAs were negative.

Example 5

Stability of Exosomal miRNA Profiles

Figure 7:
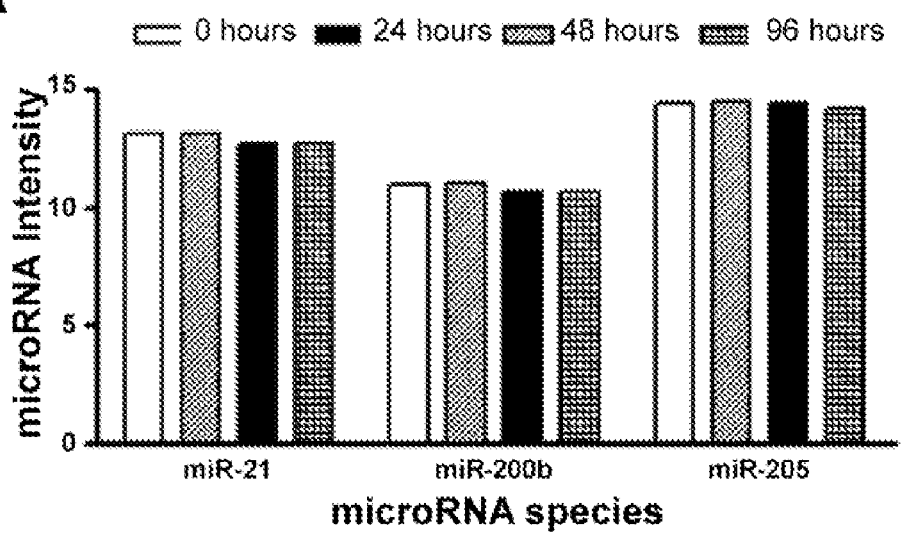
FIGS. 7A and 7B are graphs showing a comparison of specific exosomal miRNAs derived from the serum of an ovarian cancer patient, immediately after blood draw or 24, 48, and 96 hours later with sera stored at 4° C.
Figure 7:
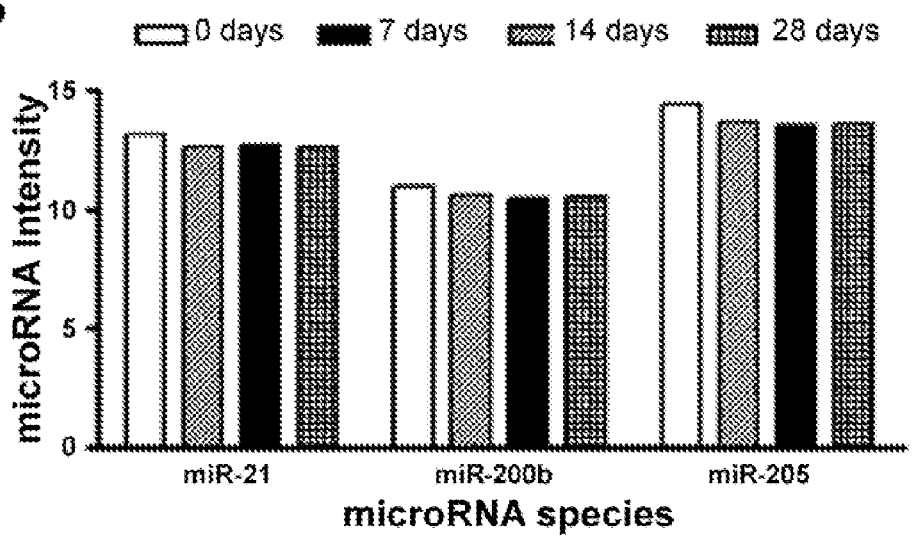

Since the measurement of circulating exosomal miRNA has been demonstrated herein to be diagnostic, the technical question of its stability was next addressed. When the miRNA profiles were performed on serum samples stored over short time periods at 4° C. (up to 96 hours) and the intensities compared (FIG. 7A), no significant differences were observed in the 3 diagnostic miRNAs analyzed. When the serum samples were stored at −70° C. for longer time intervals, the intensities of these miRNAs on the microarrays were not significantly different (FIG. 7B). These results indicate that the levels of these exosomal miRNAs were stable and do not significantly change with storage.

Discussion of Examples 1-5

MicroRNA expression profiling can be used as diagnostic tools for cancers that currently lack reliable molecular markers, such as ovarian cancer. While previous studies have indicated that miRNA signatures could serve as diagnostic and prognostic markers for ovarian cancer, these data were based on their expression in tissue specimens. The present Examples provide data demonstrating for the first time association of miRNA with circulating tumor-derived exosomes. In previous studies, miRNAs have been demonstrated to be aberrantly expressed in human ovarian cancers and the overall miRNA expression could differentiate normal versus cancer tissues (Iorio et al., 2007). The study of Lu et al. (2005) demonstrated the use of miRNA signatures as an important advance in cancer diagnosis. Their work indicated that miRNA-based identification of cancers was superior in correctly diagnosing cancer of unknown primaries than mRNA classification. However, prior to the presently-disclosed subject matter, it was not possible to use miRNA profiling in the absence of a mass to be biopsied.

Our original electron microscopic characterization of exosomes indicated that they were hollow (i.e. absence of viral-like structures) (Taylor & Black, 1986). As a result, our group, together with others, focused on external protein components of exosomes and the biologic consequences of exosome exposure. In the present Examples, however, we surprisingly demonstrate for the first time the presence of small RNA species associated with circulating tumor exosomes (FIG. 4). This small RNA lacks the 18S and 28S associated with RNA from cells. Further, microarray analysis disclosed herein demonstrated that at least part of the small RNA identified is miRNA.

The miRNA expression profiles of our ovarian tumor cells confirmed the miRNA aberrations reported in previous studies. Analyses of both circulating tumor exosomes and the tumor cells from the same patients demonstrated that both were positive for 46% of the tested miRNAs (218/467). When the intensities of the miRNA were normalized, most of these miRNAs were expressed at similar levels between the cells and exosomes or were elevated within the exosomes (175 were not significantly different and 31 were elevated within exosomes). Thus, the aberrantly expressed miRNAs, used to establish cancer-specific signatures, appear in both cellular and exosomal compartments of ovarian cancer patients.

Our comparison of specific miRNAs, previously demonstrated to be diagnostic, indicated a high degree of correlation between the miRNA from the tumor and its corresponding exosomes (ranging from 0.71 to 0.90). This high correlation even holds for miRNAs that appeared to be present at higher proportions in exosomes, such as for miR-214. The uniform elevation of specific miRNAs in exosomes has lead to the suggestion that compartmentalization of miRNAs into exosomes, for at least some miRNAs, is an active (selective) process. Such a process could be mediated by components, such as nucleolin or nucleophosmin, which are aberrantly expressed on tumor exosomes.

Since these results demonstrated that exosomal miRNA profiling can be used as a surrogate for tissue miRNA and the goal in screening would be the identification of early stage disease, the ability to detect circulating exosomal miRNAs in early stage disease was examined. The exosomal miRNA expressions of the diagnostic miRNAs between patients with early versus late stage ovarian cancers were not significantly different for most of these miRNAs (FIG. 6). miR-200c and miR-214 were lower in patients with stage I, compared to stages II and III; however, in all cases, these miRNAs were significantly elevated over the levels detected in exosomes derived from benign disease. The small RNA fraction could not be demonstrated in normal controls and attempts to assess the presence of miRNAs were negative. Thus, the absence of exosomes and/or exosomal small RNA is associated with normal, non-cancer-bearing individuals and exosomal miRNA mirroring normal tissue miRNA profiles appear to be associated with benign disease. The similarity across the stages of ovarian cancer is likely the result of standardization of starting exosomal small RNA quantities and the normalization of the resulting array data. Despite this standardization and normalization, the profiles obtained with exosomal miRNA from patients with benign disease remained distinct. These results demonstrate that the analyses of specific miRNAs associated with circulating exosomes can be applied to all stages of ovarian cancer and that benign and malignant diseases appear distinguishable based on the levels of the 8 specific miRNAs noted herein.

The miRNA signatures of exosomes parallel that of the miRNA expression profiles of the originating tumor cells, indicating that miRNA profiling can be performed in the absence of tissue and accurately reflect the tumor's profile. We also have observed that tumor derived exosomes from lung cancer patients contain miRNA that is similar to the corresponding tumor miRNA signatures (see Example 6). Circulating tumor derived exosomes can be isolated using tumor markers, such as EpCAM, followed by analysis of exosome-associated miRNA. Since this approach is non-invasive, in that it does not require a mass to be biopsied, exosomal miRNA profiling can be utilized as a screening tool for the detection of many different cancers. As specific miRNAs associated with tumor tissues are identified that predict prognosis, including therapeutic resistance (such as let-71, miR-16, miR-21 and miR-214) (Yang et al., 2008; Blower et al., 2008), their presence in tumor exosomes can also be assessed to further define the utility of exosomal miRNA profiling as a prognostic indicator. The use of exosomal miRNA profiling can extend this approach to screening of asymptomatic individuals, as well as for monitoring disease recurrence.

Example 6

Correlation of miRNA with Peripheral Blood-Derived Lung Tumor Exosomes Compared with miRNA Isolated from their Corresponding Lung Tumors In studies demonstrating diagnostic miRNA signatures of non-small cell lung carcinoma (NSCLC), specific miRNAs were overexpressed compared with normal lung tissue (miR-17-3p, miR-21, miR-106a, miR-146, miR-155, miR-191, miR-192, miR-203, miR-205, miR-210, miR-212, and miR-214). To correlate these findings with patient-derived material, miRNA fractions were isolated and profiled from circulating tumor exosomes and the original tumor using methods disclosed herein above and shown in FIG. 8. The isolated miRNAs were 3'-end labeled with Cy3 using the mirVana miRNA Array Labeling Kit. MiRNA profiling was performed in duplicate, using microarrays containing probes for 467 human mature miRNA. After hybridization, the miRNA arrays were scanned using a GenePix 4000A array scanner and the raw data normalized and analyzed using GeneSpring 7.0 Software (Silicon Genetics, Redwood City, Calif.). Normalization was performed by expressing each miRNA replicate relative to control microRNA (Ambion) added to each sample, allowing comparisons between chips.

Figure 9:
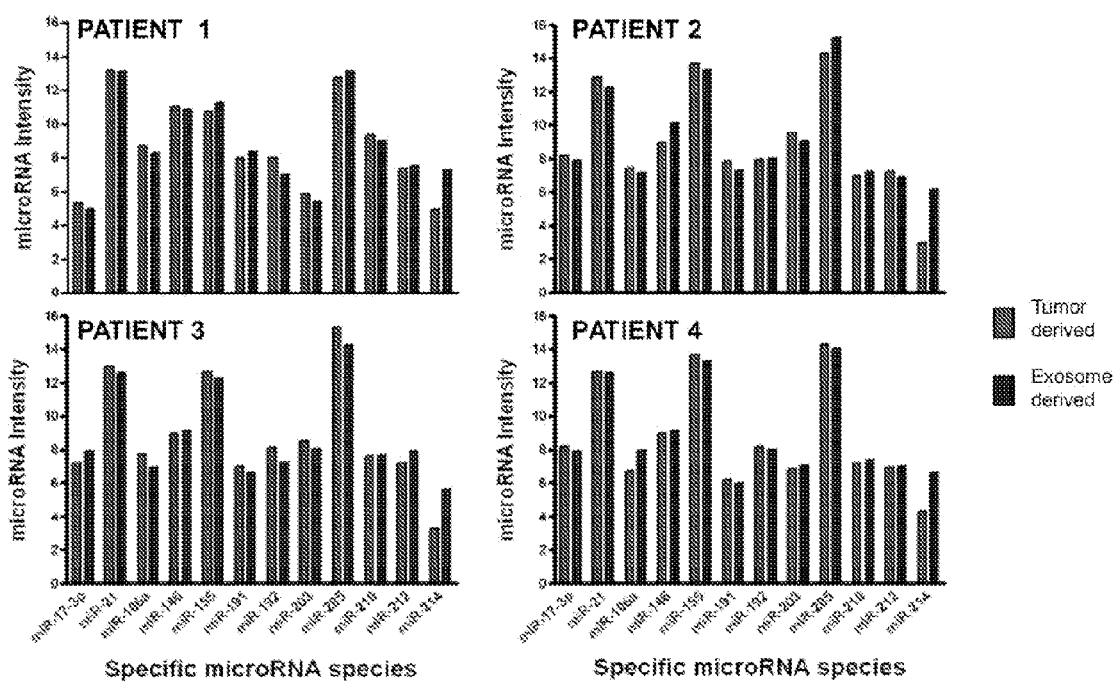
FIG. 9 is a series of graphs showing intensities for specific miRNAs derived from the advanced staged lung tumors (light gray) and from EpCAM-positive exosomes (dark gray) isolated from the sera of these same patients. Each bar presents the average intensities of duplicate samples with the results of four representative patients presented.

Comparisons between peripheral circulation-derived tumor exosomes and tumors indicated that the miRNA signatures were not significantly different (FIG. 9). This approach confirmed that at least the 12 specific miRNA were elevated in NSCLC and that the associations of these 12 were mirrored in the circulating tumor-derived exosomes. Thus, the assessment of these miRNAs can be used as a surrogate for their levels in the tumor and therefore are diagnostic for the presence of cancer, and in this particular case, NSCLC.

Example 7

Placenta-Derived Exosomal miRNA Profiling for Correlation with Adverse Pregnancy Outcomes In order to determine whether circulating exosomes comprise miRNA that can be diagnostic for adverse pregnancy outcomes (e.g., preterm birth), serum samples from pregnant subjects were collected and exosome fractions derived from placental tissues were isolated using anti-placental alkaline phosphatase antibodies linked with magnetic beads. miRNAs were isolated and profiled from the isolated circulating placenta-derived exosomes and directly from the placental tissue from the same subject as disclosed herein above and as shown in FIG. 8. Briefly, the isolated miRNAs were 3'-end labeled with Cy3 using the mirVana miRNA Array Labeling Kit. MiRNA profiling was performed in duplicate, using microarrays containing probes for 467 human mature miRNA. After hybridization, the miRNA arrays were scanned using a Gene-Pix 4000A array scanner and the raw data normalized and analyzed using GeneSpring 7.0 Software (Silicon Genetics, Redwood City, Calif.). Normalization was performed by expressing each miRNA replicate relative to control microRNA (Ambion) added to each sample, allowing comparisons between chips.

Results are set forth in Table 3. DT1 samples are miRNA isolated from placental tissue from women who carried to term. DT2 samples are miRNA isolated from placenta-derived exosomes from women who carried to term. DT3 samples are miRNA isolated from placental tissue from women who delivered preterm (delivery before 32 weeks gestation). DT4 samples are miRNA isolated from placenta-derived exosomes from women who delivered preterm. Shaded cells indicate presence in sample of miRNA tested.

These data demonstrate that miRNA profiling of placenta-derived exosomes was achieved and that these data correlate with miRNA profiles from the placenta. As such, the miRNA profiles from miRNA isolated from exosomes produced by placental cells can be utilized for diagnostic purposes of adverse pregnancy outcomes.

TABLE 3

DETECTION AND QUANTITATION OF miRNA
FROM PERIPHERAL BLOOD-DERIVED PLACENTAL
EXOSOMES AND RELATED PLACENTAL TISSUE*

| Normalized Threshold | | 3.11 | 3.14 | 4.26 | 4.85 |
|---|---|---|---|---|---|
| Normalized TPT95 | | 4.61 | 5.07 | 5.53 | 5.20 |
| | | DT1 | DT2 | DT3 | DT4 |
| Name | ID | 866A | 866B | 866C | 866D |
| hsa-miR-296 | 1098 | 5.05 | 4.33 | 4.24 | 4.79 |
| hsa-miR-330 | 1002 | 2.98 | 3.09 | 4.1 | 1.08 |
| hsa-miR-20A | 1007 | 11.46 | 11.35 | 12 | 11.93 |
| hsa-miR-28 | 1024 | 9.4 | 10.05 | 9.19 | 9.23 |
| hsa-miR-302c | 1032 | -0.58 | 3.08 | 3.5 | 1.08 |
| hsa-miR-302a | 1036 | 2.17 | 3.66 | 3.47 | 4.33 |
| hsa-miR-214 | 1057 | 6.58 | 3.93 | 6.17 | 2.99 |
| hsa-miR-99b | 1063 | 9.59 | 10.08 | 9.86 | 9.16 |
| hsa-miR-99a | 1068 | 3.81 | 4.53 | 7.34 | 6.46 |
| hsa-miR-10a | 1072 | 10.1 | 10.76 | 9.63 | 9.55 |
| hsa-let-7d | 1085 | 12.53 | 13.32 | 12.65 | 12.5 |
| hsa-miR-138 | 1089 | 5.37 | 5.26 | 4.18 | 3.61 |
| hsa-miR-140 | 1106 | 3.23 | 4.3 | 2.01 | 0.58 |
| hsa-miR-23a | 1114 | 14.51 | 15.08 | 14.99 | 14.78 |
| hsa-miR-215 | 1122 | 0.71 | 1.79 | 0.51 | 1.38 |
| hsa-miR-183 | 1127 | 9.08 | 9.63 | 8.99 | 8.9 |
| hsa-miR-32 | 1135 | 2 | 2.49 | 2.42 | 0.58 |
| hsa-miR-25 | 1139 | 11.34 | 11.3 | 12.23 | 12.01 |
| hsa-miR-218 | 1143 | 2.71 | 3.37 | 4.61 | 5.33 |
| hsa-miR-107 | 1163 | 11.68 | 12.18 | 11.29 | 11.31 |
| hsa-miR-145 | 1168 | 1.74 | 2.38 | 3.47 | 1.38 |
| hsa-miR-181a | 1172 | 11.9 | 12.62 | 11.35 | 11.15 |
| hsa-miR-125a | 1193 | 12.34 | 13.07 | 11.67 | 11.84 |
| hsa-miR-222 | 1198 | 12.37 | 12.53 | 11.77 | 10.99 |
| hsa-miR-372 | 1105 | -0.58 | 3.08 | 2.51 | 1.08 |
| hsa-miR-9* | 1232 | -0.58 | -0.01 | 0.51 | 0.58 |
| hsa-miR-142-3p | 1253 | 2.72 | 3.06 | 4.59 | 3.91 |
| hsa-miR-198 | 1258 | 4.2 | 3.92 | 3.32 | 3.67 |
| hsa-miR-196a | 1263 | 4.78 | 5.07 | 3.42 | 4.04 |
| hsa-miR-16 | 1272 | 12.28 | 12.05 | 12.98 | 12.6 |
| hsa-miR-200a | 1287 | 8.29 | 8.72 | 7.17 | 7.44 |
| hsa-miR-18a | 1292 | 6.41 | 6.66 | 7.98 | 8.5 |
| hsa-miR-101 | 1297 | 4.62 | 4.87 | 5.55 | 6.01 |
| hsa-miR-195 | 1311 | 6.09 | 6.58 | 6.03 | 6.43 |
| hsa-miR-136 | 1203 | 3.69 | 3.77 | 3.52 | 3.65 |
| hsa-miR-153 | 1225 | 1.71 | 2.08 | 0.51 | 0.58 |
| hsa-miR-31 | 1227 | 8.97 | 9.49 | 9.6 | 9.32 |
| hsa-miR-184 | 1242 | -0.08 | -0.51 | 3.1 | 0.58 |
| hsa-miR-33 | 1274 | 2.01 | 3.66 | 3.58 | 3.75 |
| hsa-miR-147 | 1278 | 4.65 | 2.95 | 3.47 | 3.17 |
| hsa-miR-106b | 1282 | 9.47 | 9.19 | 10.59 | 10.38 |
| hsa-miR-212 | 1288 | 2.67 | 1.81 | 2.89 | 3.75 |
| hsa-miR-15a | 1312 | 9.92 | 10.12 | 10.79 | 11.06 |
| hsa-miR-135b | 1331 | 4.51 | 4.03 | 4.42 | 4.07 |
| hsa-miR-92 | 1335 | 12.29 | 12.63 | 12.62 | 12.26 |
| hsa-miR-342 | 1349 | 9.14 | 9.62 | 8.36 | 8.39 |
| hsa-miR-205 | 1368 | 6.15 | 5.74 | 15.25 | 14.33 |
| hsa-miR-150 | 1385 | 4.02 | 2.87 | 3.33 | 1.38 |
| hsa-miR-149 | 1392 | 6.23 | 5.65 | 5.92 | 4.79 |
| hsa-let-7b | 1431 | 12.73 | 12.43 | 13.73 | 14.06 |
| hsa-miR-370 | 1445 | 4.14 | 3.7 | 4.37 | 2.58 |
| hsa-miR-206 | 1449 | 5.22 | 4.34 | 5.58 | 4.91 |
| hsa-miR-128a | 1350 | 7.54 | 7.9 | 8.06 | 8.01 |
| hsa-miR-197 | 1487 | 11.05 | 9.76 | 10.03 | 9.28 |
| hsa-miR-182 | 1506 | 10.11 | 10.89 | 10.09 | 10.41 |
| hsa-miR-553 | 1750 | 2.77 | 2.95 | 4.05 | 3.17 |
| hsa-miR-606 | 1758 | -0.58 | -0.51 | 1.01 | 0.58 |
| hsa-miR-518f | 1762 | 1 | -0.01 | 2.51 | 0.58 |
| hsa-miR-519d | 1766 | 2.17 | 3.28 | 0.51 | 3.04 |
| hsa-miR-520g | 1770 | -0.58 | 1.9 | 3.51 | 2.49 |

TABLE 3-continued

DETECTION AND QUANTITATION OF miRNA FROM PERIPHERAL BLOOD-DERIVED PLACENTAL EXOSOMES AND RELATED PLACENTAL TISSUE*

| | | | | | |
|---|---|---|---|---|---|
| hsa-miR-520e | 1774 | -0.58 | 1.79 | 0.51 | 3.75 |
| hsa-miR-329 | 1778 | 2.67 | 2.08 | 3.32 | 2.91 |
| hsa-miR-634 | 1782 | 6.69 | 2.64 | 3.32 | 1.08 |
| hsa-miR-614 | 1786 | 1.21 | -0.01 | 1.31 | 2.91 |
| hsa-miR-596 | 1794 | -0.58 | -0.51 | 0.51 | 0.58 |
| hsa-miR-182* | 1457 | -0.08 | -0.51 | 0.51 | 0.58 |
| hsa-miR-223 | 1467 | 2.71 | 2.49 | 4.17 | 3.17 |
| hsa-miR-512-5p | 1843 | -0.58 | 0.79 | 2.51 | 0.58 |
| hsa-miR-643 | 1855 | -0.08 | -0.51 | 0.51 | 2.91 |
| hsa-miR-591 | 1859 | 0.21 | 1.29 | 0.51 | 0.58 |
| hsa-miR-485-5p | 1863 | 4.27 | 2.49 | 2.6 | 0.58 |
| hsa-miR-369-5p | 1867 | 2 | 1.49 | 0.51 | 0.58 |
| hsa-miR-575 | 1871 | 2.75 | 2.69 | 4.36 | 3.75 |
| hsa-miR-626 | 1879 | -0.58 | 0.29 | 0.51 | 0.58 |
| hsa-miR-650 | 1883 | -0.08 | -0.51 | 3.68 | 0.58 |
| hsa-miR-663 | 1891 | 5.41 | 5 | 6.17 | 5.76 |
| hsa-miR-520f_hsa-miR-520c | 1802 | 1.61 | 1.79 | 2.97 | 3.15 |
| hsa-miR-382 | 1806 | 4.48 | 4.14 | 4.04 | 3.25 |
| hsa-miR-656 | 1810 | -0.58 | 0.29 | 2.83 | 0.58 |
| hsa-miR-605 | 1814 | 1.08 | -0.51 | 1.31 | 0.58 |
| hsa-miR-655 | 1920 | 1.21 | 2.3 | 2.1 | 3.17 |
| hsa-miR-545 | 1932 | 2.5 | 2.66 | 2.92 | 3.58 |
| hsa-miR-502 | 1940 | 3.46 | 4.16 | 4.99 | 3.75 |
| hsa-miR-200a* | 1952 | 5.35 | 5.86 | 3.42 | 2.25 |
| hsa-miR-640 | 1956 | 2.24 | -0.51 | 2.51 | 0.58 |
| hsa-miR-620 | 1960 | -0.58 | -0.51 | 0.51 | 1.08 |
| hsa-miR-514 | 1972 | 2 | 2.95 | 1.01 | 1.38 |
| hsa-miR-583 | 1980 | -0.58 | -0.51 | 0.51 | 0.58 |
| hsa-miR-548b | 1988 | 1.92 | -0.01 | 2.51 | 0.58 |
| hsa-miR-609 | 1899 | 2.55 | 2.58 | 3.6 | 3.54 |
| hsa-miR-563 | 1903 | -0.58 | -0.51 | 0.51 | 0.58 |
| hsa-miR-377 | 1929 | 1.74 | -0.01 | 2.6 | 0.58 |
| hsa-miR-376a | 1933 | -0.58 | 0.29 | 0.51 | 0.58 |
| hsa-miR-433 | 1937 | 2.71 | 2.19 | 3.74 | 1.08 |
| hsa-miR-500 | 1957 | 4.67 | 4.88 | 6.34 | 5.8 |
| hsa-miR-652 | 1961 | 6.26 | 6.6 | 5.52 | 5.05 |
| hsa-miR-384 | 1969 | -0.58 | 2.3 | 0.51 | 0.58 |
| hsa-miR-548d | 1977 | -0.58 | 2.3 | 0.51 | 0.58 |
| hsa-miR-518c | 1981 | 0.92 | 1.81 | 3.68 | 1.38 |
| hsa-miR-561 | 1985 | -0.58 | 2.49 | 0.51 | 1.38 |
| hsa-miR-551a | 2018 | 3.77 | 3.27 | 4.06 | 3.91 |
| hsa-miR-554 | 2026 | -0.08 | 0.29 | 1.01 | 1.08 |
| hsa-miR-510 | 2030 | 2.59 | -0.51 | 0.51 | 0.58 |
| hsa-miR-525 | 2034 | -0.58 | 2.06 | 3.1 | 0.58 |
| hsa-miR-570 | 2054 | -0.58 | -0.51 | 0.51 | 0.58 |
| hsa-miR-617 | 2062 | 2 | 2.49 | 0.51 | 2.91 |
| hsa-miR-556 | 2070 | -0.58 | 1.81 | 1.31 | 1.08 |
| hsa-miR-551b | 2074 | 1.37 | 1.79 | 3.97 | 3.38 |
| hsa-miR-424 | 1993 | 5.87 | 5.84 | 4.54 | 4.79 |
| hsa-miR-612 | 1997 | 2.87 | 0.29 | 2.83 | 0.58 |
| hsa-miR-130a | 2005 | 8.07 | 8.66 | 9.08 | 9.2 |
| hsa-miR-569 | 2110 | -0.58 | -0.51 | 0.51 | 0.58 |
| hsa-miR-302a* | 2114 | -0.58 | 1.95 | 0.51 | 0.58 |
| hsa-miR-499 | 2122 | -0.58 | -0.01 | 1.01 | 0.58 |
| hsa-miR-429 | 2134 | 5.68 | 5.39 | 3.89 | 4.83 |
| hsa-miR-365 | 2138 | 8.7 | 8.73 | 7.51 | 7.31 |
| hsa-miR-598 | 2150 | -0.58 | 0.29 | 0.51 | 0.58 |
| hsa-miR-29a | 2154 | 13.45 | 13.83 | 12.21 | 12.27 |
| hsa-miR-503 | 2162 | 5.44 | 6.25 | 1.31 | 4.39 |
| hsa-miR-624 | 2166 | -0.58 | 1.99 | 0.51 | 3.39 |
| hsa-miR-409-5p | 2089 | -0.58 | -0.51 | 0.51 | 0.58 |
| hsa-miR-550 | 2097 | 4.34 | 4.26 | 3.89 | 2.58 |
| hsa-miR-627 | 2101 | -0.58 | 1.49 | 0.51 | 0.58 |
| hsa-miR-33b | 2105 | -0.58 | 0.29 | 0.51 | 0.58 |
| hsa-miR-581 | 2227 | 2.32 | 1.65 | 2.31 | 0.58 |
| hsa-miR-493-3p | 2231 | 2.17 | 0.29 | 0.51 | 0.58 |
| hsa-miR-610 | 2239 | 4.57 | -0.51 | 0.51 | 0.58 |
| hsa-miR-516-3p | 2259 | -0.58 | -0.51 | 0.51 | 0.58 |
| hsa-miR-422a | 2263 | 8.33 | 8.48 | 9.59 | 9.25 |
| hsa-miR-449 | 2267 | 2.91 | 2.48 | 1.31 | 0.58 |
| hsa-miR-585 | 2271 | 3.58 | 3.74 | 4.51 | 4.12 |
| hsa-miR-379 | 2275 | 2.22 | -0.51 | 0.51 | 0.58 |
| hsa-miR-92b | 2182 | 7.86 | 8.04 | 7.75 | 7.13 |
| hsa-miR-629 | 2316 | 6.12 | 5.93 | 6.82 | 7.03 |
| hsa-miR-580 | 2320 | -0.58 | 1.49 | 0.51 | 2.58 |
| hsa-miR-448 | 2324 | 1.74 | -0.51 | 2.83 | 0.58 |
| hsa-miR-659 | 2328 | -0.58 | 0.29 | 0.51 | 0.58 |
| hsa-miR-592 | 2332 | 0.21 | 2.95 | 2.83 | 0.58 |
| hsa-miR-587 | 2336 | -0.58 | -0.51 | 0.51 | 0.58 |
| hsa-miR-671 | 2839 | 4.15 | 3.98 | 4.21 | 0.58 |
| hsa-miR-802 | 2851 | 1.42 | -0.51 | 0.51 | 0.58 |
| hsa-miR-767-3p | 2863 | 1.42 | 2.3 | 2.51 | 0.58 |
| hsa-miR-608 | 2279 | 3.74 | 1.29 | 2.47 | 0.58 |

TABLE 3-continued

DETECTION AND QUANTITATION OF miRNA FROM PERIPHERAL BLOOD-DERIVED PLACENTAL EXOSOMES AND RELATED PLACENTAL TISSUE*

| | | | | | |
|---|---|---|---|---|---|
| hsa-miR-668 | 2287 | 1.21 | -0.51 | 0.51 | 0.58 |
| hsa-miR-210 | 2291 | 9.13 | 8.6 | 8.39 | 7.96 |
| hsa-miR-26a | 2299 | 12.6 | 12.61 | 12.27 | 12.73 |
| hsa-miR-493-5p | 2329 | 2 | 2.65 | 2.17 | 1.08 |
| hsa-miR-202* | 2337 | 2.55 | 2.08 | 3.32 | 1.88 |
| hsa-miR-454-5p | 2840 | 11.51 | 11.6 | 12.87 | 13.07 |
| hsa-miR-770-5p | 2844 | 2.24 | -0.01 | 1.01 | 0.58 |
| hsa-miR-767-5p | 2848 | -0.58 | -0.51 | 0.51 | 0.58 |
| hsa-miR-769-3p | 2865 | 3.8 | 3.74 | 3.01 | 2.88 |
| hsa-miR-758 | 2869 | -0.58 | -0.51 | 0.51 | 0.58 |
| hsa-miR-765 | 2864 | 5.35 | 5.13 | 6.08 | 5.77 |
| hsa-miR-301 | 1103 | 3.96 | 4.08 | 4.04 | 4.68 |
| hsa-miR-191 | 1017 | 9.84 | 10.87 | 11.01 | 10.9 |
| hsa-miR-93 | 1029 | 9.68 | 9.58 | 10.93 | 9.75 |
| hsa-let-7f | 1033 | 11.59 | 12.43 | 11.79 | 11.94 |
| hsa-miR-373 | 1037 | 3.54 | 2.4 | 4.51 | 3.08 |
| hsa-miR-200b | 1042 | 10.9 | 11.07 | 10.17 | 9.02 |
| hsa-miR-100 | 1064 | 7.25 | 6.69 | 7.81 | 5.54 |
| hsa-miR-324-3p | 1082 | 5.67 | 4.71 | 5.64 | 3.99 |
| hsa-miR-34b | 1096 | 3.27 | 3.49 | 3.83 | 4.54 |
| hsa-miR-324-5p | 1115 | 3.84 | 2.29 | 4.16 | 4.49 |
| hsa-miR-199a* | 1124 | 1.82 | 2.24 | 1.01 | 4.17 |
| hsa-miR-103 | 1164 | 11.27 | 10.65 | 11.3 | 9.18 |
| hsa-miR-142-5p | 1169 | -0.58 | -0.51 | 2.31 | 0.58 |
| hsa-miR-220 | 1173 | 3.67 | 3.04 | 4.26 | 3.99 |
| hsa-miR-151 | 1199 | 9.73 | 9.47 | 10.22 | 10.45 |
| hsa-miR-186 | 1141 | 4.72 | 4.93 | 3.86 | 4.49 |
| hsa-miR-128b | 1153 | 6.29 | 6.26 | 6.7 | 6.1 |
| hsa-miR-130b | 1165 | 7.72 | 6.96 | 7.99 | 6.49 |
| hsa-miR-338 | 1174 | 2.42 | 2.66 | 2.67 | 2.91 |
| hsa-miR-199b | 1178 | 1.98 | -0.01 | 3.67 | 3.46 |
| hsa-miR-125b | 1182 | 9.34 | 8.81 | 9.86 | 8.11 |
| hsa-miR-124a | 1213 | 1.74 | -0.51 | 0.51 | 0.58 |
| hsa-miR-122a | 1243 | 5.11 | 3.49 | 4.97 | 4.71 |
| hsa-miR-30d | 1251 | 11.72 | 11.93 | 11.32 | 11.69 |
| hsa-miR-203 | 1260 | 1.42 | 2.9 | 9.1 | 9.56 |
| hsa-let-7c | 1268 | 11.91 | 12.72 | 13.09 | 12.47 |
| hsa-miR-216 | 1294 | 2 | 2.45 | 2.71 | 3.38 |
| hsa-miR-144 | 1300 | 0.71 | 0.49 | 1.01 | 2.91 |
| hsa-miR-15b | 1313 | 11.75 | 12.27 | 12.66 | 12.77 |
| hsa-miR-192 | 1205 | 7.05 | 8.48 | 6 | 6.14 |
| hsa-miR-133a | 1215 | 3.27 | 3.07 | 3.82 | 4.11 |
| hsa-miR-126 | 1380 | 6.42 | 6.42 | 5.94 | 7.51 |
| hsa-miR-326 | 1393 | 3.32 | 0.29 | 0.51 | 3.17 |
| hsa-miR-98 | 1423 | 6.58 | 7.21 | 6.9 | 7.33 |
| hsa-let-7g | 1432 | 10.8 | 11.21 | 10.01 | 10.06 |
| hsa-miR-190 | 1437 | 3.16 | 3.57 | 4.02 | 4.29 |
| hsa-miR-189 | 1442 | 2.59 | 2.79 | 2.92 | 3.38 |
| hsa-miR-137 | 1339 | 2.66 | 3.06 | 4.36 | 3.88 |
| hsa-miR-105 | 1345 | 2.37 | 2.48 | 4.32 | 3.17 |
| hsa-miR-96 | 1507 | 4.66 | 4.17 | 4.58 | 4.58 |
| hsa-miR-518b | 1759 | -0.58 | -0.51 | 0.51 | 0.58 |
| hsa-miR-519e | 1767 | -0.08 | 2.3 | 2.83 | 1.08 |
| hsa-miR-520a | 1771 | 1.42 | 1.99 | 3.1 | 0.58 |
| hsa-miR-552 | 1779 | -0.58 | -0.51 | 0.51 | 0.58 |
| hsa-miR-451 | 1783 | 1 | -0.51 | 3.32 | 2.58 |
| hsa-miR-523 | 1787 | -0.58 | -0.51 | 0.51 | 0.58 |
| hsa-miR-518e | 1795 | -0.08 | -0.51 | 2.83 | 0.58 |
| hsa-miR-299-5p | 1458 | 1.74 | 2.06 | 2.51 | 0.58 |
| hsa-miR-95 | 1482 | 3.94 | 3.78 | 2.71 | 3.08 |
| hsa-miR-520h | 1824 | 1.74 | 1.08 | 0.51 | 0.58 |
| hsa-miR-593 | 1832 | 4.92 | 1.08 | 4.1 | 2.91 |
| hsa-miR-574 | 1840 | 11.34 | 9.36 | 11.12 | 9.45 |
| hsa-miR-641 | 1856 | -0.58 | -0.51 | 0.51 | 0.58 |
| hsa-miR-504 | 1860 | -0.58 | 1.81 | 0.51 | 0.58 |
| hsa-miR-202 | 1864 | 2.59 | 1.9 | 2.97 | 3.67 |
| hsa-miR-564 | 1884 | 0.42 | -0.51 | 0.51 | 0.58 |
| hsa-miR-604 | 1892 | 1.71 | -0.51 | 2.83 | 0.58 |
| hsa-miR-519b | 1799 | -0.08 | 3.49 | 3.97 | 3.83 |
| hsa-miR-520d | 1803 | 2.58 | 3.56 | 3.89 | 4.36 |
| hsa-miR-602 | 1825 | -0.58 | -0.51 | 0.51 | 0.58 |
| hsa-miR-622 | 1829 | 1.42 | 2.66 | 0.51 | 1.38 |
| hsa-miR-483 | 1845 | 8.06 | 3.91 | 7.36 | 4.34 |
| hsa-miR-600 | 1853 | 0.21 | -0.01 | 0.51 | 2.38 |
| hsa-miR-631 | 1861 | -0.58 | -0.51 | 0.51 | 0.58 |
| hsa-miR-383 | 1865 | 2.17 | 1.95 | 0.51 | 1.88 |
| hsa-miR-29b | 1869 | 6.67 | 6.05 | 5.9 | 6.65 |
| hsa-miR-613 | 1881 | 2.42 | -0.01 | 1.31 | 0.58 |
| hsa-miR-453 | 1904 | 3.93 | 3.59 | 4.76 | 4.17 |
| hsa-miR-489 | 1908 | -0.58 | -0.51 | 0.51 | 0.58 |
| hsa-miR-23b | 1930 | 13.2 | 13.81 | 12.99 | 13.61 |
| hsa-miR-376b | 1934 | -0.58 | -0.01 | 0.51 | 0.58 |

TABLE 3-continued

DETECTION AND QUANTITATION OF miRNA FROM PERIPHERAL BLOOD-DERIVED PLACENTAL EXOSOMES AND RELATED PLACENTAL TISSUE*

| | | | | | |
|---|---|---|---|---|---|
| hsa-miR-501 | 1942 | 2.87 | 2.72 | 1.31 | 3.25 |
| hsa-miR-517c | 1946 | 3.01 | 3.02 | 4.36 | 4.39 |
| hsa-miR-516-5p | 1950 | -0.08 | -0.51 | 1.01 | 0.58 |
| hsa-miR-548c | 1978 | -0.58 | -0.51 | 1.01 | 1.08 |
| hsa-miR-625 | 1897 | 6.54 | 7.16 | 5.67 | 5.65 |
| hsa-miR-630 | 1905 | 2.74 | 1.49 | 2.92 | 3.49 |
| hsa-miR-644 | 1913 | 0.21 | 2.29 | 2.51 | 2.91 |
| hsa-miR-488 | 2015 | -0.58 | 0.29 | 0.51 | 0.58 |
| hsa-miR-633 | 2023 | 1.42 | -0.51 | 0.51 | 0.58 |
| hsa-miR-527 | 2039 | 3.42 | 1.87 | 2.51 | 1.08 |
| hsa-miR-589 | 2055 | -0.08 | -0.51 | 1.31 | 0.58 |
| hsa-miR-508 | 2071 | 2.81 | 2.79 | 3.21 | 4.04 |
| hsa-miR-566 | 2075 | -0.58 | -0.51 | 0.51 | 0.58 |
| hsa-miR-449b | 2083 | 2.41 | 2.48 | 3.97 | 2.58 |
| hsa-miR-603 | 1990 | 4.74 | 2.84 | 3.76 | 0.58 |
| hsa-miR-607 | 2111 | -0.58 | -0.51 | 0.51 | 0.58 |
| hsa-miR-559 | 2115 | -0.58 | 0.29 | 0.51 | 0.58 |
| hsa-miR-506 | 2123 | -0.58 | -0.51 | 0.51 | 0.58 |
| hsa-miR-200c | 2131 | 4.25 | 3.75 | 13.3 | 13.7 |
| hsa-miR-29c | 2155 | 2.75 | 3.24 | 3.6 | 4.2 |
| hsa-miR-411 | 2167 | -0.58 | -0.51 | 0.51 | 0.58 |
| hsa-miR-381 | 2171 | -0.58 | -0.51 | 0.51 | 0.58 |
| hsa-miR-455 | 2179 | 2.87 | 2.52 | 2.6 | 0.58 |
| hsa-miR-363* | 2086 | 1.42 | -0.51 | 0.51 | 0.58 |
| hsa-miR-380-5p | 2090 | 0.21 | -0.51 | 0.51 | 0.58 |
| hsa-miR-567 | 2094 | -0.58 | -0.51 | 0.51 | 0.58 |
| hsa-miR-378 | 2208 | 2.24 | 2.3 | 3.6 | 2.58 |
| hsa-miR-638 | 2212 | 7.37 | 6.34 | 8.56 | 7.57 |
| hsa-miR-542-5p | 2216 | 1.42 | -0.51 | 0.51 | 0.58 |
| hsa-miR-518f* | 2220 | -0.58 | -0.51 | 3.17 | 3.67 |
| hsa-miR-549 | 2232 | -0.58 | -0.51 | 0.51 | 0.58 |
| hsa-miR-558 | 2240 | -0.58 | -0.51 | 0.51 | 0.58 |
| hsa-let-7i | 2244 | 12.8 | 13.03 | 10.86 | 10.79 |
| hsa-miR-560 | 2256 | -0.58 | -0.51 | 0.51 | 0.58 |
| hsa-miR-636 | 2260 | -0.58 | -0.51 | 0.51 | 3.17 |
| hsa-miR-422b | 2264 | 9.17 | 8.72 | 10.51 | 10.23 |
| hsa-miR-193b | 2268 | 9.68 | 8.44 | 8.63 | 7.54 |
| hsa-miR-491 | 2272 | 1.74 | 0.79 | 2.81 | 0.58 |
| hsa-miR-484 | 2191 | 8.32 | 7.81 | 8.29 | 7.72 |
| hsa-miR-662 | 2199 | -0.58 | -0.51 | 0.51 | 0.58 |
| hsa-miR-623 | 2203 | 1.74 | 2.45 | 0.51 | 0.58 |
| hsa-miR-486 | 2209 | 3.86 | 3.3 | 4.2 | 4.6 |
| hsa-miR-639 | 2213 | 1.87 | 1.49 | 2.31 | 1.38 |
| hsa-miR-517a_hsa-miR-517b | 2217 | 2.11 | 2.56 | 3.87 | 3.28 |
| hsa-miR-645 | 2221 | 3.12 | 1.29 | 0.51 | 2.58 |
| hsa-miR-653 | 2229 | -0.58 | -0.51 | 0.51 | 0.58 |
| hsa-miR-146b | 2237 | 5.56 | 5.29 | 4.21 | 5.59 |
| hsa-miR-571 | 2249 | 3.33 | 2.99 | 4.1 | 2.91 |
| hsa-miR-191* | 2257 | 2.42 | 2.95 | 1.31 | 0.58 |
| hsa-miR-7 | 2261 | 2.44 | 3.02 | 2.51 | 3.54 |
| hsa-miR-647 | 2269 | 4.95 | 4.27 | 5.5 | 6.01 |
| hsa-miR-637 | 2273 | 4.65 | 2.84 | 4.9 | 4.17 |
| hsa-miR-30b | 2280 | 9.94 | 9.87 | 9.86 | 9.66 |
| hsa-miR-431 | 2288 | 1.74 | -0.01 | 0.51 | 2.58 |
| hsa-miR-452 | 2292 | 4.68 | 5.15 | 5.14 | 5.85 |
| hsa-miR-361 | 2296 | 10.36 | 11.32 | 10.53 | 10.83 |
| hsa-miR-576 | 2314 | 1.87 | -0.51 | 2.83 | 0.58 |
| hsa-miR-432 | 2326 | 3.74 | 3.47 | 3.51 | 2.58 |
| hsa-miR-375 | 2342 | 3.42 | 2.15 | 0.51 | 3.75 |
| hsa-miR-766 | 2841 | 9.66 | 6.37 | 8.18 | 7.59 |
| hsa-miR-768-3p | 2845 | 9.89 | 9.61 | 9.2 | 9.48 |
| hsa-miR-769-5p | 2861 | 4.03 | 4.07 | 4.47 | 3.46 |
| hsa-miR-542-3p | 2289 | -0.58 | -0.51 | 0.51 | 0.58 |
| hsa-miR-513 | 2301 | 3.8 | 2.56 | 3.97 | 4.38 |
| hsa-miR-362 | 2017 | 2.93 | 4.53 | 4.88 | 4.38 |
| hsa-miR-325 | 2025 | -0.58 | -0.51 | 0.51 | 0.58 |
| hsa-miR-520a* | 2033 | -0.58 | -0.51 | 0.51 | 0.58 |
| hsa-miR-517* | 2037 | -0.58 | -0.51 | 0.51 | 0.58 |
| hsa-miR-565 | 2045 | 7.04 | 4.89 | 5.13 | 6.45 |
| hsa-miR-526b | 2049 | -0.58 | -0.51 | 0.51 | 0.58 |
| hsa-miR-30e-3p | 2053 | 8.97 | 9.4 | 7.84 | 7.61 |
| hsa-miR-601 | 2088 | 2.87 | -0.51 | 0.51 | 0.58 |
| hsa-miR-519a | 2104 | -0.58 | 1.49 | 0.51 | 1.08 |
| hsa-miR-632 | 2108 | -0.08 | 2.3 | 0.51 | 0.58 |
| hsa-miR-320 | 1005 | 12.75 | 13.28 | 13.11 | 13.09 |
| hsa-miR-132 | 1014 | 4.94 | 6.57 | 6.22 | 7.04 |
| hsa-miR-193a | 1018 | 4.56 | 4.32 | 3.66 | 4.58 |
| hsa-miR-22 | 1022 | 8.71 | 8.95 | 8.69 | 8.79 |
| hsa-miR-224 | 1026 | 6.69 | 7.1 | 6.4 | 6.96 |
| hsa-let-7a | 1030 | 13.37 | 14.07 | 14.63 | 14.91 |
| hsa-miR-302d | 1034 | 2.32 | 2.74 | 3.76 | 3.28 |
| hsa-miR-369-3p | 1038 | 2.72 | 2.38 | 4.68 | 3.83 |
| hsa-miR-154* | 1047 | -0.58 | -0.51 | 0.51 | 0.58 |

TABLE 3-continued

DETECTION AND QUANTITATION OF miRNA FROM PERIPHERAL BLOOD-DERIVED PLACENTAL EXOSOMES AND RELATED PLACENTAL TISSUE*

| | | | | | |
|---|---|---|---|---|---|
| hsa-miR-368 | 1059 | 1.42 | 0.49 | 0.51 | 0.58 |
| hsa-miR-373* | 1078 | -0.58 | -0.51 | 0.51 | 0.58 |
| hsa-miR-34c | 1095 | 1.42 | 1.49 | 0.51 | 2.99 |
| hsa-miR-154 | 1101 | 1.61 | -0.51 | 1.31 | 2.75 |
| hsa-miR-106a | 1006 | 12.01 | 12.48 | 12.09 | 12.36 |
| hsa-miR-181c | 1015 | 5.67 | 6.09 | 4.64 | 4.27 |
| hsa-miR-17-5p | 1031 | 11.57 | 11.85 | 11.34 | 11.83 |
| hsa-miR-302b | 1035 | -0.08 | 2.66 | 3.26 | 4.04 |
| hsa-miR-19b | 1039 | 10.14 | 10.07 | 11.3 | 11.47 |
| hsa-miR-24 | 1044 | 12.91 | 13.2 | 13.13 | 13.4 |
| hsa-miR-367 | 1052 | 2.17 | -0.01 | 1.01 | 0.58 |
| hsa-miR-17-3p | 1079 | 4.95 | 5.02 | 4.83 | 5.34 |
| hsa-miR-221 | 1088 | 13.67 | 13.73 | 12.88 | 12.76 |
| hsa-miR-335 | 1146 | -0.58 | -0.51 | 6.66 | 7.68 |
| hsa-miR-323 | 1154 | -0.58 | 1.81 | 0.51 | 0.58 |
| hsa-miR-199a | 1167 | 2.31 | -0.51 | 0.51 | 3.17 |
| hsa-miR-126* | 1171 | 3.12 | 1.95 | 3.68 | 3.15 |
| hsa-miR-337 | 1175 | 2.22 | -0.51 | 3.97 | 2.91 |
| hsa-miR-181a* | 1179 | 5.67 | 5.34 | 5.91 | 5.76 |
| hsa-miR-331 | 1183 | 6.46 | 5.25 | 5.55 | 4.95 |
| hsa-miR-340 | 1187 | 2.96 | 2.99 | 3.86 | 4.17 |
| hsa-miR-208 | 1108 | 1.42 | -0.51 | 0.51 | 0.58 |
| hsa-miR-188 | 1116 | 3.94 | 3.31 | 3.86 | 4.39 |
| hsa-miR-9 | 1231 | 2.96 | 3.25 | 4 | 4.53 |
| hsa-miR-34a | 1235 | 6.95 | 6.56 | 7.17 | 7.33 |
| hsa-miR-30c | 1252 | 13.78 | 13.97 | 12.46 | 12.24 |
| hsa-miR-19a | 1271 | 5.93 | 5.76 | 8.01 | 8.36 |
| hsa-miR-371 | 1276 | 3.67 | 2.19 | 3.36 | 3.38 |
| hsa-miR-10b | 1301 | 6.91 | 7.36 | 7.73 | 8.03 |
| hsa-miR-21 | 1315 | 13.13 | 13.2 | 12.28 | 12.88 |
| hsa-miR-217 | 1206 | 2.53 | 2.49 | 0.51 | 3.57 |
| hsa-miR-302b* | 1210 | 1.87 | 2.49 | 2.51 | 2.99 |
| hsa-miR-135a | 1216 | 2.41 | 3.62 | 3.47 | 3.89 |
| hsa-miR-148a | 1361 | 3 | 1.45 | 6.87 | 7.35 |
| hsa-miR-339 | 1366 | 4.85 | 4.26 | 5.12 | 5.2 |
| hsa-miR-187 | 1381 | 3.69 | 2.4 | 4.21 | 3.75 |
| hsa-miR-346 | 1390 | 5.77 | 3.2 | 4.09 | 4.87 |
| hsa-miR-146a | 1409 | 9.7 | 9.88 | 7.17 | 7.56 |
| hsa-miR-143 | 1415 | -0.58 | -0.51 | 2.51 | 3.75 |
| hsa-miR-219 | 1426 | 2 | 1.81 | 3.32 | 4.04 |
| hsa-miR-185 | 1451 | 8.4 | 8.73 | 9.33 | 9.46 |
| hsa-miR-328 | 1455 | 7.15 | 4.5 | 4.92 | 4.33 |
| hsa-miR-196b | 1321 | 4.65 | 4.44 | 5.08 | 5.68 |
| hsa-miR-204 | 1489 | 0.71 | 2.49 | 0.51 | 1.38 |
| hsa-miR-133b | 1498 | -0.58 | -0.51 | 0.51 | 0.58 |
| hsa-miR-129 | 1512 | 6.33 | 6.08 | 7.2 | 8.02 |
| hsa-miR-649 | 1756 | 3.32 | 2.93 | 3.17 | 2.17 |
| hsa-miR-518a | 1760 | -0.58 | -0.51 | 0.51 | 0.58 |
| hsa-miR-562 | 1764 | -0.58 | -0.51 | 0.51 | 1.08 |
| hsa-miR-526b* | 1772 | -0.58 | -0.51 | 0.51 | 0.58 |
| hsa-miR-522 | 1776 | 2.87 | 3.4 | 5.74 | 5.87 |
| hsa-miR-490 | 1784 | -0.58 | -0.51 | 0.51 | 0.58 |
| hsa-miR-618 | 1788 | 2.22 | 1.65 | 0.51 | 1.08 |
| hsa-miR-525* | 1796 | -0.58 | 1.49 | 1.31 | 0.58 |
| hsa-miR-30a-5p | 1460 | 12.45 | 12.55 | 11.09 | 11.04 |
| hsa-miR-302c* | 1474 | 0.42 | -0.01 | 0.51 | 0.58 |
| hsa-miR-27a | 1485 | 11.64 | 11.67 | 11.97 | 12.27 |
| hsa-miR-30a-3p | 1505 | 12.22 | 12.57 | 10 | 10.48 |
| hsa-miR-494 | 1753 | 4.47 | 3.87 | 6.12 | 5.48 |
| hsa-miR-518d | 1761 | -0.58 | 2.08 | 0.51 | 0.58 |
| hsa-miR-519c | 1765 | -0.08 | 0.29 | 0.51 | 3.75 |
| hsa-miR-20b | 1769 | 10.41 | 10.8 | 10.92 | 11.2 |
| hsa-miR-520b | 1773 | -0.08 | 1.49 | 1.01 | 2.58 |
| hsa-miR-495 | 1777 | -0.58 | -0.51 | 0.51 | 2.91 |
| hsa-miR-521 | 1785 | 3.42 | 0.49 | 3.31 | 3.75 |
| hsa-miR-646 | 1793 | -0.58 | -0.51 | 0.51 | 0.58 |
| hsa-miR-648 | 1804 | -0.58 | -0.51 | 0.51 | 0.58 |
| hsa-miR-410 | 1808 | 1.42 | -0.51 | 0.51 | 1.08 |
| hsa-miR-487a | 1812 | -0.58 | -0.51 | 0.51 | 0.58 |
| hsa-miR-409-3p | 1820 | -0.58 | -0.51 | 1.01 | 0.58 |
| hsa-miR-363 | 1822 | -0.58 | -0.51 | 3.32 | 1.08 |
| hsa-miR-181b | 1830 | 11.53 | 11.96 | 10.84 | 11.02 |
| hsa-miR-616 | 1842 | 2.22 | -0.51 | 0.51 | 2.49 |
| hsa-miR-18a* | 1850 | 4.52 | 2.99 | 4.97 | 3.83 |
| hsa-miR-635 | 1854 | -0.58 | -0.51 | 1.31 | 0.58 |
| hsa-miR-423 | 1874 | 8.9 | 8.85 | 9.09 | 8.46 |
| hsa-miR-611 | 1882 | -0.58 | -0.51 | 0.51 | 0.58 |
| hsa-miR-524 | 1797 | -0.58 | -0.51 | 0.51 | 0.58 |
| hsa-miR-595 | 1805 | 9.11 | 6.55 | 8.47 | 6.49 |
| hsa-miR-487b | 1817 | 4.65 | 4.3 | 5.22 | 5.53 |
| hsa-miR-425-3p | 1943 | 4.14 | 4.02 | 3.39 | 3.96 |
| hsa-miR-594 | 1951 | 10.94 | 10.48 | 11.55 | 11.22 |

TABLE 3-continued

DETECTION AND QUANTITATION OF miRNA FROM PERIPHERAL BLOOD-DERIVED PLACENTAL EXOSOMES AND RELATED PLACENTAL TISSUE*

| | | | | | |
|---|---|---|---|---|---|
| hsa-miR-532 | 1959 | 5.87 | 5.79 | 6.62 | 6.14 |
| hsa-miR-568 | 1963 | -0.58 | -0.51 | 0.51 | 1.38 |
| hsa-miR-496 | 1967 | -0.58 | -0.51 | 0.51 | 0.58 |
| hsa-miR-544 | 1971 | 1.08 | 2.49 | 1.01 | 2.91 |
| hsa-miR-509 | 1975 | -0.08 | -0.51 | 0.51 | 3.75 |
| hsa-miR-548a | 1979 | -0.58 | -0.51 | 0.51 | 0.58 |
| hsa-miR-658 | 1894 | -0.58 | -0.51 | 1.01 | 0.58 |
| hsa-miR-555 | 1898 | 1.42 | -0.51 | 0.51 | 0.58 |
| hsa-miR-657 | 1902 | -0.58 | -0.51 | 0.51 | 1.38 |
| hsa-miR-512-3p | 1910 | 2.56 | 2.74 | 4.41 | 3.83 |
| hsa-miR-524* | 2024 | -0.58 | -0.51 | 0.51 | 0.58 |
| hsa-miR-515-5p | 2032 | -0.58 | -0.51 | 0.51 | 0.58 |
| hsa-miR-526a | 2036 | -0.58 | -0.51 | 5.78 | 5.87 |
| hsa-miR-619 | 2044 | 2.01 | 1.49 | 1.01 | 4.08 |
| hsa-miR-578 | 2048 | 3.54 | 2.79 | 3.17 | 2.38 |
| hsa-miR-573 | 2056 | -0.58 | 2.08 | 0.51 | 0.58 |
| hsa-miR-492 | 2060 | -0.08 | 1.49 | 2.71 | 2.67 |
| hsa-miR-590 | 2064 | 3.27 | 3.4 | 5.51 | 5.08 |
| hsa-miR-515-3p | 2068 | 1.74 | 2.88 | 3.51 | 1.08 |
| hsa-miR-621 | 2076 | -0.58 | -0.51 | 0.51 | 0.58 |
| hsa-miR-539 | 2080 | 2.74 | 1.81 | 2.51 | 4.28 |
| hsa-miR-497 | 1995 | 3.05 | 3.11 | 3.26 | 0.58 |
| hsa-miR-152 | 2007 | 7.72 | 8.44 | 6.59 | 7.2 |
| hsa-miR-181d | 2011 | 8.56 | 8.9 | 7.83 | 7.49 |
| hsa-miR-660 | 2144 | 5.3 | 5.36 | 6.62 | 6.8 |
| hsa-miR-526c | 2152 | -0.58 | -0.51 | 2.42 | 0.58 |
| hsa-miR-584 | 2176 | 10.1 | 10.43 | 7.6 | 7.99 |
| hsa-miR-299-3p | 2180 | 1.42 | -0.51 | 0.51 | 0.58 |
| hsa-miR-376a* | 2087 | -0.58 | -0.51 | 0.51 | 0.58 |
| hsa-miR-597 | 2107 | -0.58 | -0.51 | 0.51 | 0.58 |
| hsa-miR-511 | 2109 | 2.59 | -0.01 | 2.83 | 2.91 |
| hsa-miR-599 | 2113 | -0.58 | -0.51 | 0.51 | 0.58 |
| hsa-miR-141 | 2117 | -0.58 | -0.51 | 7.91 | 8.21 |
| hsa-miR-18b | 2125 | 5.18 | 5.41 | 6.65 | 6.98 |
| hsa-miR-582 | 2141 | -0.58 | -0.51 | 4.9 | 4.87 |
| hsa-miR-577 | 2153 | -0.58 | -0.51 | 0.51 | 0.58 |
| hsa-miR-586 | 2173 | 2.11 | 1.49 | 2.47 | 1.08 |
| hsa-miR-380-3p | 2177 | -0.58 | -0.51 | 0.51 | 0.58 |
| hsa-miR-505 | 2184 | 5.06 | 5.45 | 4.16 | 4.58 |
| hsa-miR-485-3p | 2196 | 3.74 | -0.51 | 0.51 | 0.58 |
| hsa-miR-642 | 2200 | 4.22 | 1.15 | 2.42 | 0.58 |
| hsa-miR-615 | 2204 | 3.94 | -0.01 | 0.51 | 0.58 |
| hsa-miR-572 | 2206 | -0.58 | -0.51 | 0.51 | 0.58 |
| hsa-miR-520d* | 2218 | -0.58 | -0.51 | 0.51 | 0.58 |
| hsa-miR-628 | 2222 | 3.59 | 2.19 | 2.17 | 3.83 |
| hsa-miR-518c* | 2226 | 0.21 | -0.51 | 0.51 | 0.58 |
| hsa-miR-425-5p | 2234 | 8.86 | 9.29 | 9.01 | 8.92 |
| hsa-miR-432* | 2266 | -0.58 | -0.51 | 0.51 | 0.58 |
| hsa-miR-661 | 2274 | 2.42 | 1.81 | 0.51 | 0.58 |
| hsa-miR-421 | 2185 | 4.06 | 5.49 | 6.41 | 6.43 |
| hsa-miR-452* | 2193 | -0.58 | -0.51 | 0.51 | 0.58 |
| hsa-miR-27b | 2303 | 10.82 | 11.2 | 11.39 | 11.55 |
| hsa-miR-412 | 2307 | 2.59 | -0.01 | 0.51 | 2.58 |
| hsa-miR-579 | 2311 | -0.58 | -0.01 | 0.51 | 0.58 |
| hsa-miR-519e* | 2315 | -0.58 | -0.51 | 0.51 | 0.58 |
| hsa-miR-588 | 2327 | 1.42 | -0.51 | 0.51 | 0.58 |
| hsa-miR-651 | 2335 | 1.71 | 1.69 | 3.39 | 2.91 |
| hsa-miR-557 | 2339 | 3.37 | 2.49 | 3.51 | 0.58 |
| hsa-miR-507 | 2343 | -0.58 | 0.29 | 0.51 | 3.39 |
| hsa-miR-801 | 2846 | 5.97 | 3.08 | 4.59 | 1.88 |
| hsa-miR-768-5p | 2854 | 8.68 | 8.01 | 8.5 | 8.38 |
| hsa-miR-454-3p | 2858 | 3 | 3.37 | 4.32 | 3.78 |
| hsa-miR-654 | 2278 | 2.22 | -0.51 | 1.31 | 0.58 |
| hsa-miR-498 | 2298 | 2.87 | -0.51 | 0.51 | 2.67 |
| hsa-miR-148b | 1362 | 6.83 | 6.76 | 6.82 | 6.69 |
| hsa-miR-211 | 1367 | 3.56 | -0.51 | 0.51 | 0.58 |
| hsa-miR-127 | 1377 | 1.8 | -0.51 | 0.51 | 0.58 |
| hsa-miR-139 | 1384 | -0.58 | -0.51 | 0.51 | 0.58 |
| hsa-miR-194 | 1416 | 8.57 | 8.28 | 4.64 | 5.81 |
| hsa-let-7e | 1421 | 7.42 | 9.18 | 8.74 | 9.52 |
| hsa-miR-345 | 1444 | 4.63 | 4.62 | 3.68 | 3.17 |
| hsa-miR-1 | 1448 | -0.58 | 0.29 | 0.51 | 0.58 |
| hsa-miR-30e-5p | 1461 | -0.58 | -0.51 | 0.51 | 0.58 |
| hsa-miR-134 | 1470 | -0.58 | -0.51 | 0.51 | 0.58 |
| hsa-miR-155 | 1476 | 8.21 | 9.31 | 4.32 | 6.17 |
| hsa-miR-374 | 1480 | 1.42 | 1.79 | 0.51 | 1.38 |
| hsa-miR-26b | 1484 | 9.52 | 10 | 9.72 | 10.43 |

*Raw data was background-subtracted, Log2-transformed, and normalized
Intensity for each oligo probe is based on averaging of duplicate spots
Data for all 467 human oligo probes is shown
Normalized threshold is calculated based on log2(5* stdev of non-spot background + trim mean negative control probe signal)
Normalized threshold is calculated based on 95th percentile of negative control probe signal
Total of 236 Human Probes are Above Threshold in at least 1 sample.
Total of 158 Human Probes are Above TPT95 in at least 1 sample.

The present Examples demonstrate the successful application of a diagnostic assay for cancer and adverse pregnancy outcomes having a greatly improved specificity, sensitivity and positive predictive value over currently available diagnostics and also provide additional information on stage, grade, and therapeutic response that is unavailable in any other assay format.

REFERENCES

Andre F, Schartz N E, Movassagh M, et al. Malignant effusions and immunogenic tumour-derived exosomes. Lancet 2002; 360: 295-305.

Bard M P, Hegmans J P, Hemmes A, et al. Proteomic analysis of exosomes isolated from human malignant pleural effusions. Am J Respir Cell Mol Biol 2004; 31:114-21.

Bartel D P. MicroRNAs: Genomics, biogenesis, mechanism, and function. Cell 2004; 116:281-97.

Berek J S, Schultes B C Nicodemus C F. Biologic and immunologic therapies for ovarian cancer. J Clin Oncol 2003; 21(s10):168-74.

Calin G A, Croce C M. MicroRNA-cancer connection: the beginning of a new tale. Cancer Res 2006a; 66:7390-94.

Calin G A, Croce C M. MicroRNA signatures in human cancers. Nature Rev Cancer 2006b; 6:857-66.

Choi D S, Lee J M, Park G W, et al. Proteomic analysis of microvesicles derived from human colorectal cancer cells. J Proteome Res 2007; 6:4646-55.

De Cecco L, Marchionni L, Gariboldi M, Reid J F, Lagonigro M S, Caramuta S, et al. Gene expression profiling of advanced ovarian cancer: Characteristization of a molecular signature involving fibroblast growth factor 2. Oncogene 2004; 23:8171-83.

Esquela-Kerscher A, Slack F J. Oncomirs—microRNAs with a role in cancer. Nature Rev Cancer 2006; 6:259-69.

Heijnen H F G, Schiel A E, Fijnheer R, Geuze H J, Sixma J J. Activation platelets release two types of membrane vesicles: Microvesicles by surface shedding and exosomes derived from exocytosis of multivesicular bodies and alpha granules. Blood 1999; 94:3791-9.

Iorio M V, Visone R, Di Leva G, Donati V, Petrocca F, Casalini P, et al. MicroRNA signatures in human ovarian cancer. Cancer Res 2007; 67:8699-707.

J. M. Escola J M, Kleijmeer M J, Stoorvogel W, Griffith J M, Yoshie O, Geuze H J. Selective enrichment of tetraspan proteins on the internal vesicles of multivesicular endosomes and on exosomes secreted by human B-lymphocytes. Biol Chem 1998; 273: 20121-7.

Koga K, Matsumoto K, Akiyoshi T, Kubo M, et al. Purification, characterization and biological significance of tumor-derived exosomes, Anticancer Res 2005; 25: 3703-7.

Lu J, Getz G, Miska E A, Alvarez-Saavedra E, Lamb J, Peck D, et al. MicroRNA expression profiles classify human cancers. Nature 2005; 435: 834-8.

Mears R, Craven R A, Hanrahan S, et al. Proteomic analysis of melanoma-derived exosomes by two-dimensional polyacrylamide gel electrophoresis and mass spectrometry. Proteomics 2004; 4:4019-31.

Menon U, Jacobs I J. Recent developments in ovarian cancer screening. Curr Opin Obstet Gynecol 2000; 12:39-42.

Miska E A. How microRNAs control cell division, differentiation, and death. Curr Opi. Genet Dev 2005; 5:563-8.

Olver C, Vidal M, Proteomic analysis of secreted exosomes. Subcell Biochem. 2007; 43:99-131.

Paul E. Blower P E, Chung J H, Verducci J S, Lin S, Park J K, Dai Z, Liu C G, Schmittgen T D, Reinhold W C, Croce C M, Weinstein J N, Sadee W. MicroRNAs modulate the chemosensitivity of tumor cells. Mol Cancer Therap 2008; 7: 1-9.

Raposo G, Tenza D, Mecheri S, Peronet R, Bonnerot C, Desaymard C. Accumulation of major histocompatibility complex class II molecules in mast cell secretory granules and their release upon degranulation. Mol Biol Cell 1997; 8:2631-45.

Ratajczak J, Miekus K, Kucia M, et al. Embryonic stem cell-derived microvesicles reprogram hematopoietic progenitors: Evidence for horizontal transfer of mRNA and protein delivery. Leukemia 2006; 20: 847-56.

Sabapatha A, Gercel-Taylor C, Taylor D D. Specific isolation of placental-derived exosomes from the circulation of pregnant women and their immunoregulatory consequences. Am J. Reprod Immunol 2006, 56:345-55.

Sankaranarayanan R, Ferlay J. Worldwide burden of gynaecological cancer: the size of the problem. Best Pract Res Clin Obstet & Gynaecol 2006; 20:207-25.

Taylor D D, Doellgast G J. Quantitation of □eroxidise-antibody binding to membrane fragments using column chromatography. Anal Biochem 1979; 98:53-9.

Taylor D D, Homesley H D, Doellgast G J. Binding of specific peroxidise-labeled antibody to placental-type alkaline phosphatase on tumor-derived membrane fragments. Cancer Res 1980: 40:4964-69.

Taylor D D, Black P H. Shedding of plasma membrane fragments: Neoplastic and developmental importance. In: *Developmental Biology*, (M. Steinberg, ed.) vol. 3, 1986: 33-57.

Taylor D D, Gercel-Taylor C. Tumour-derived exosomes as mediates of T-cell signaling defects. Brit J Cancer 2005; 92:305-11.

Taylor, D. D., Bohler, H. C., Gercel-Taylor, C. Pregnancy-linked suppression of TcR signaling pathways by a circulating factor absent in recurrent spontaneous pregnancy loss. Molecular Immunology 2006, 43: 1872-80.

Valadi, H, Ekstrom K, Bossius A, Sjostrand M, Lee J J, Lotvall J O. Exosome-mediated transfer of mRNA and microRNA is a novel mechanism of genetic exchange. Nature Cell. Biol. 2007; 9:652-9.

Valenti R, Huber V, Filipazzi P, Pilla L, Sovena G, Villa A et al. Human tumor-released microvesicles promote the differentiation of myeloid cells with transforming growth factor-beta-mediated suppressive activity on T lymphocytes. Cancer Res 2006; 66: 9290-8.

Yang H, Kong W, He L, Zhao J J, O'Donnell J D, Wang J, Wenham W M, Coppola D, Kruk P A, Nicosia S V, Cheng J Q. MicroRNA expression profiling in human ovarian cancer: miR-214 induces cell survival and cisplatin resistance by targeting PTEN. Cancer Res 2008; 68: 425-33.

Zhang L, Huang J, Yang N, et al. microRNAs exhibit high frequency genomic alterations in human cancer. Proc Natl Acad Sci USA 2006; 103:9136-41.

What is claimed is:

1. A method for assessing the presence of one or more microRNAs in microvesicles, comprising isolating a population of cancer-derived microvesicles from a biological sample using a microvesicle surface marker, isolating microRNA from said population of cancer-derived microvesicles and determining a presence of one or more microRNAs in said cancer-derived microvesicles.

2. A method of determining the presence of one or more bio-markers in microvesicles, comprising: isolating a population of cancer-derived extracellular microvesicles from a biological sample; isolating microRNA from said population of cancer-derived extracellular microvesicles and determining an expression profile of one or more microRNA; and comparing the expression profile with a profile from a selected reference sample to determine a presence of one or more biomarkers in the microvesicles.

3. The method of claim 1, wherein the biological sample is from a human.

4. The method of claim 1, wherein the biological sample comprises milk, blood, serum, plasma, ascites, cyst fluid, pleural fluid, peritoneal fluid, cerebral spinal fluid, tears, urine, saliva, sputum, or combinations thereof.

5. The method of claim 1, wherein the surface marker is EpCAM.

6. The method of claim 1, wherein the surface marker is selected from a group consisting of EpCAM, Fas ligand, PD-1, MICA/B, mdr 1, MMPs, CD44, autoreactive antigens, tetraspanins, and MHC class I molecule.

7. The method of claim 1, wherein said determining step comprises labeling the one or more microRNAs with a detectable label.

8. The method of claim 1, wherein said determining comprises capturing the one or more microRNAs with one or more polynucleotide probes that selectively bind each of the one or more microRNAs.

9. The method of claim 1, wherein said determining comprises using a real-time polymerase chain reaction.

10. The method of claim 1, wherein the one or more microRNAs comprise one or more microRNAs set forth in Table 1.

11. The method of claim 1, wherein the one or more microRNAs comprise one or more microRNAs set forth in Table 2.

12. The method of claim 1, wherein the isolating comprises using size exclusion chromatography, filtration or immunosorbent capture.

13. The method of claim 1, wherein the microRNA comprises one or more microRNAs selected from the group consisting of miR-21, miR-141, miR-200a, miR-200b, miR-200c, miR-203, miR-205, and miR-214.

14. The method of claim 2, wherein the biological sample is from a human.

15. The method of claim 2, wherein the biological sample comprises milk, blood, serum, plasma, ascites, cyst fluid, pleural fluid, peritoneal fluid, cerebral spinal fluid, tears, urine, saliva, sputum, or combinations thereof.

16. The method of claim 2, wherein said determining step comprises labeling the one or more microRNAs with a detectable label.

17. The method of claim 2, wherein said determining comprises capturing the one or more microRNAs with one or more polynucleotide probes that selectively bind each of the one or more microRNAs.

18. The method of claim 2, wherein said determining comprises using a real-time polymerase chain reaction.

19. The method of claim 2, wherein the one or more microRNAs comprise one or more microRNAs set forth in Table 1.

20. The method of claim 2, wherein the one or more microRNAs comprise one or more microRNAs set forth in Table 2.

21. The method of claim 2, wherein the isolating comprises using size exclusion chromatography, filtration or immunosorbent capture.

22. The method of claim 2, wherein the microRNA comprises one or more microRNAs selected from the group consisting of miR-21, miR-141, miR-200a, miR-200b, miR-200c, miR-203, miR-205, and miR-214.

23. The method of claim 9, wherein the surface marker is EpCAM.

24. The method of claim 9, wherein the surface marker is selected from a group consisting of EpCAM, Fas ligand, PD-1, MICA/B, mdr 1, MMPs, CD44, autoreactive antigens, tetraspanins, and MHC class I molecule.

* * * * *